US011806602B2

(12) United States Patent
Kuo

(10) Patent No.: US 11,806,602 B2
(45) Date of Patent: Nov. 7, 2023

(54) SEQUENTIAL MOUTH GUARD

(71) Applicant: Align Technology, Inc., San Jose, CA (US)

(72) Inventor: Eric Kuo, San Jose, CA (US)

(73) Assignee: Align Technology, Inc., San Jose, CA (US)

( * ) Notice: Subject to any disclaimer, the term of this patent is extended or adjusted under 35 U.S.C. 154(b) by 0 days.

(21) Appl. No.: 15/788,529

(22) Filed: Oct. 19, 2017

(65) Prior Publication Data

US 2018/0036623 A1 Feb. 8, 2018

Related U.S. Application Data

(62) Division of application No. 12/277,191, filed on Nov. 24, 2008, now abandoned.

(51) Int. Cl.
*A61F 5/00* (2006.01)
*A63B 71/08* (2006.01)
(Continued)

(52) U.S. Cl.
CPC .............. *A63B 71/085* (2013.01); *A61C 7/08* (2013.01); *A61F 5/566* (2013.01); *A63B 2071/088* (2013.01)

(58) Field of Classification Search
CPC .... A61C 7/08; A61C 7/36; A61C 5/14; A61C 7/00; A63B 2071/086; A63B 2071/088;
(Continued)

(56) References Cited

U.S. PATENT DOCUMENTS 2,192,558 A 3/1940 Poindexter
2,467,432 A 4/1949 Kesling
(Continued)

FOREIGN PATENT DOCUMENTS

AU 3031677 A 5/1979
AU 517102 B2 7/1981
(Continued)

OTHER PUBLICATIONS

AADR. American Association for Dental Research, Summary of Activities, Mar. 20-23, 1980, Los Angeles, CA, p. 195.
(Continued)

*Primary Examiner* — Adam Baker
(74) *Attorney, Agent, or Firm* — FORTEM IP LLP

(57) ABSTRACT

The present invention provides protective repositioning appliances, accommodating mouth guards, and covering guards that protect an orthodontic patient against impact-induced injuries, as well as related systems and methods. A protective appliance can include teeth receiving cavities shaped to receive and reposition a patient's teeth and can include an occlusal portion having an impact-absorbing compliance. An accommodating mouth guard can include teeth receiving cavities shaped to accommodate a patient's teeth from a first arrangement to a second arrangement and can include an occlusal portion having an impact-absorbing compliance. A covering guard can include a guard segment that covers at least a portion of an appliance. The combination of a guard segment and an appliance can provide an occlusal compliance that absorbs impacts.

20 Claims, 16 Drawing Sheets

(51) Int. Cl.
*A61C 7/08* (2006.01)
*A61F 5/56* (2006.01)

(58) Field of Classification Search
CPC .......... A63B 71/085; A61F 5/56; A61F 5/566; A61F 2005/563
USPC ........... 433/5–8, 24; 128/848, 859, 861, 862
See application file for complete search history.

(56) References Cited

U.S. PATENT DOCUMENTS

| | | | |
|---|---|---|---|
| 2,531,222 A | 11/1950 | Kesling | |
| 2,966,908 A | 1/1961 | Cathcart et al. | |
| 3,107,668 A * | 10/1963 | Thompson | A63B 71/085 128/861 |
| 3,407,500 A | 10/1968 | Kesling | |
| 3,600,808 A | 8/1971 | Reeve | |
| 3,660,900 A | 5/1972 | Andrews | |
| 3,683,502 A | 8/1972 | Wallshein | |
| 3,738,005 A | 6/1973 | Cohen et al. | |
| 3,860,803 A | 1/1975 | Levine | |
| 3,916,526 A | 11/1975 | Schudy | |
| 3,922,786 A | 12/1975 | Lavin | |
| 3,943,924 A * | 3/1976 | Kallestad | A63B 71/085 128/861 |
| 3,950,851 A | 4/1976 | Bergersen | |
| 3,983,628 A | 10/1976 | Acevedo | |
| 4,014,096 A | 3/1977 | Dellinger | |
| 4,063,552 A | 12/1977 | Going et al. | |
| 4,195,046 A | 3/1980 | Kesling | |
| 4,253,828 A | 3/1981 | Coles et al. | |
| 4,324,546 A | 4/1982 | Heitlinger et al. | |
| 4,324,547 A | 4/1982 | Arcan et al. | |
| 4,348,178 A | 9/1982 | Kurz | |
| 4,448,735 A | 5/1984 | Huge | |
| 4,478,580 A | 10/1984 | Barrut | |
| 4,500,294 A | 2/1985 | Lewis | |
| 4,504,225 A | 3/1985 | Yoshii | |
| 4,505,673 A | 3/1985 | Yoshii | |
| 4,526,540 A | 7/1985 | Dellinger | |
| 4,575,330 A | 3/1986 | Hull | |
| 4,575,805 A | 3/1986 | Moermann et al. | |
| 4,591,341 A | 5/1986 | Andrews | |
| 4,609,349 A | 9/1986 | Cain | |
| 4,611,288 A | 9/1986 | Duret et al. | |
| 4,656,860 A | 4/1987 | Orthuber et al. | |
| 4,663,720 A | 5/1987 | Duret et al. | |
| 4,664,626 A | 5/1987 | Kesling | |
| 4,676,747 A | 6/1987 | Kesling | |
| 4,715,368 A * | 12/1987 | George | A61F 5/566 128/859 |
| 4,742,464 A | 5/1988 | Duret et al. | |
| 4,755,139 A | 7/1988 | Abbatte et al. | |
| 4,763,791 A | 8/1988 | Halverson et al. | |
| 4,793,803 A * | 12/1988 | Martz | A61C 7/08 433/6 |
| 4,798,534 A | 1/1989 | Breads | |
| 4,836,778 A | 6/1989 | Baumrind et al. | |
| 4,837,732 A | 6/1989 | Brandestini et al. | |
| 4,848,365 A * | 7/1989 | Guarlotti | A63B 71/085 128/862 |
| 4,850,864 A | 7/1989 | Diamond | |
| 4,850,865 A | 7/1989 | Napolitano | |
| 4,856,991 A | 8/1989 | Breads et al. | |
| 4,877,398 A | 10/1989 | Kesling | |
| 4,880,380 A | 11/1989 | Martz | |
| 4,889,238 A | 12/1989 | Batchelor | |
| 4,890,608 A | 1/1990 | Steer | |
| 4,935,635 A | 6/1990 | O'Harra | |
| 4,936,862 A | 6/1990 | Walker et al. | |
| 4,937,928 A | 7/1990 | Van Der Zel | |
| 4,941,826 A | 7/1990 | Loran et al. | |
| 4,964,770 A | 10/1990 | Steinbichler et al. | |
| 4,975,052 A | 12/1990 | Spencer et al. | |
| 4,983,334 A | 1/1991 | Adell | |
| 5,011,405 A | 4/1991 | Lemchen | |
| 5,017,133 A | 5/1991 | Miura | |
| 5,027,281 A | 6/1991 | Rekow et al. | |
| 5,035,613 A | 7/1991 | Breads et al. | |
| 5,037,294 A | 8/1991 | Bergersen | |
| 5,055,039 A | 10/1991 | Abbatte et al. | |
| 5,059,118 A | 10/1991 | Breads et al. | |
| 5,080,007 A | 1/1992 | Maheu | |
| 5,082,007 A * | 1/1992 | Adell | A63B 71/085 128/862 |
| 5,100,316 A | 3/1992 | Wildman | |
| 5,121,333 A | 6/1992 | Riley et al. | |
| 5,125,832 A | 6/1992 | Kesling | |
| 5,128,870 A | 7/1992 | Erdman et al. | |
| 5,130,064 A | 7/1992 | Smalley et al. | |
| 5,131,843 A | 7/1992 | Hilgers et al. | |
| 5,131,844 A | 7/1992 | Marinaccio et al. | |
| 5,139,419 A | 8/1992 | Andreiko et al. | |
| 5,145,364 A | 9/1992 | Martz et al. | |
| 5,176,517 A | 1/1993 | Truax | |
| 5,184,306 A | 2/1993 | Erdman et al. | |
| 5,186,623 A | 2/1993 | Breads et al. | |
| 5,257,203 A | 10/1993 | Riley et al. | |
| 5,273,429 A | 12/1993 | Rekow et al. | |
| 5,278,756 A | 1/1994 | Lemchen et al. | |
| 5,328,362 A * | 7/1994 | Watson | A61C 7/00 128/861 |
| 5,338,198 A | 8/1994 | Wu et al. | |
| 5,340,309 A | 8/1994 | Robertson | |
| 5,342,202 A | 8/1994 | Deshayes | |
| 5,368,478 A | 11/1994 | Andreiko et al. | |
| 5,382,164 A | 1/1995 | Stern | |
| 5,395,238 A | 3/1995 | Andreiko et al. | |
| 5,431,562 A | 7/1995 | Andreiko et al. | |
| 5,440,326 A | 8/1995 | Quinn | |
| 5,440,496 A | 8/1995 | Andersson et al. | |
| 5,447,432 A | 9/1995 | Andreiko et al. | |
| 5,452,219 A | 9/1995 | Dehoff et al. | |
| 5,454,717 A | 10/1995 | Andreiko et al. | |
| 5,456,600 A | 10/1995 | Andreiko et al. | |
| 5,474,448 A | 12/1995 | Andreiko et al. | |
| RE35,169 E | 3/1996 | Lemchen et al. | |
| 5,499,633 A * | 3/1996 | Fenton | A61F 5/566 128/848 |
| 5,518,397 A | 5/1996 | Andreiko et al. | |
| 5,528,735 A | 6/1996 | Strasnick et al. | |
| 5,533,895 A | 7/1996 | Andreiko et al. | |
| 5,542,842 A | 8/1996 | Andreiko et al. | |
| 5,549,476 A | 8/1996 | Stern | |
| 5,562,448 A | 10/1996 | Mushabac | |
| 5,587,912 A | 12/1996 | Andersson et al. | |
| 5,605,459 A | 2/1997 | Kuroda et al. | |
| 5,607,305 A | 3/1997 | Andersson et al. | |
| 5,614,075 A | 3/1997 | Andre, Sr. | |
| 5,621,648 A | 4/1997 | Crump | |
| 5,624,257 A | 4/1997 | Farrell | |
| 5,636,379 A | 6/1997 | Williams | |
| 5,645,420 A | 7/1997 | Bergersen | |
| 5,645,421 A | 7/1997 | Slootsky | |
| 5,655,653 A | 8/1997 | Chester | |
| 5,683,243 A | 11/1997 | Andreiko et al. | |
| 5,683,244 A * | 11/1997 | Truax | A61C 7/36 433/24 |
| 5,692,894 A | 12/1997 | Schwartz et al. | |
| 5,725,376 A | 3/1998 | Poirier | |
| 5,725,378 A | 3/1998 | Wang | |
| 5,733,126 A | 3/1998 | Andersson et al. | |
| 5,740,267 A | 4/1998 | Echerer et al. | |
| 5,742,700 A | 4/1998 | Yoon et al. | |
| 5,799,100 A | 8/1998 | Clarke et al. | |
| 5,800,174 A | 9/1998 | Andersson | |
| 5,823,778 A | 10/1998 | Schmitt et al. | |
| 5,848,115 A | 12/1998 | Little et al. | |
| 5,857,853 A | 1/1999 | Van Nifterick et al. | |
| 5,866,058 A | 2/1999 | Batchelder et al. | |
| 5,876,199 A | 3/1999 | Bergersen | |
| 5,879,158 A | 3/1999 | Doyle et al. | |
| 5,880,961 A | 3/1999 | Crump | |
| 5,880,962 A | 3/1999 | Andersson et al. | |

(56) References Cited

U.S. PATENT DOCUMENTS

| | | | |
|---|---|---|---|
| 5,934,288 A | 8/1999 | Avila et al. | |
| 5,954,500 A * | 9/1999 | Spriggs | A61C 7/00 128/861 |
| 5,957,686 A | 9/1999 | Anthony | |
| 5,964,587 A | 10/1999 | Sato | |
| 5,971,754 A | 10/1999 | Sondhi et al. | |
| 5,975,893 A | 11/1999 | Chishti et al. | |
| 6,015,289 A | 1/2000 | Andreiko et al. | |
| 6,044,309 A | 3/2000 | Honda | |
| 6,049,743 A | 4/2000 | Baba | |
| 6,062,861 A | 5/2000 | Andersson | |
| 6,068,482 A | 5/2000 | Snow | |
| 6,099,314 A | 8/2000 | Kopelman et al. | |
| 6,123,544 A | 9/2000 | Cleary | |
| 6,152,731 A | 11/2000 | Jordan et al. | |
| 6,183,248 B1 | 2/2001 | Chishti et al. | |
| 6,190,165 B1 | 2/2001 | Andreiko et al. | |
| 6,217,325 B1 | 4/2001 | Chishti et al. | |
| 6,217,334 B1 | 4/2001 | Hultgren | |
| 6,244,861 B1 | 6/2001 | Andreiko et al. | |
| 6,309,215 B1 | 10/2001 | Phan et al. | |
| 6,315,553 B1 | 11/2001 | Sachdeva et al. | |
| 6,322,359 B1 | 11/2001 | Jordan et al. | |
| 6,350,120 B1 | 2/2002 | Sachdeva et al. | |
| 6,382,975 B1 | 5/2002 | Poirier | |
| 6,398,548 B1 | 6/2002 | Muhammad et al. | |
| 6,402,707 B1 | 6/2002 | Ernst | |
| 6,482,298 B1 | 11/2002 | Bhatnagar | |
| 6,494,210 B1 * | 12/2002 | Mams | A63B 71/085 128/859 |
| 6,524,101 B1 | 2/2003 | Phan et al. | |
| 6,554,611 B2 | 4/2003 | Chishti et al. | |
| 6,572,372 B1 | 6/2003 | Phan et al. | |
| 6,629,840 B2 | 10/2003 | Chishti et al. | |
| 6,705,861 B2 | 3/2004 | Chishti et al. | |
| 6,705,863 B2 | 3/2004 | Phan et al. | |
| 6,722,880 B2 | 4/2004 | Chishti et al. | |
| 6,790,036 B2 | 9/2004 | Graham | |
| 2002/0006597 A1 | 1/2002 | Andreiko et al. | |
| 2002/0187451 A1 * | 12/2002 | Phan | A61C 7/00 433/6 |
| 2003/0009252 A1 | 1/2003 | Pavlovskaia et al. | |
| 2003/0139834 A1 | 7/2003 | Nikolskiy et al. | |
| 2003/0207224 A1 * | 11/2003 | Lotte | A61C 7/08 433/6 |
| 2003/0224311 A1 | 12/2003 | Cronauer | |
| 2003/0224313 A1 * | 12/2003 | Bergersen | A61C 7/08 433/6 |
| 2003/0224314 A1 * | 12/2003 | Bergersen | A61C 7/08 433/6 |
| 2004/0103905 A1 | 6/2004 | Farrell | |
| 2004/0128010 A1 | 7/2004 | Pavlovskaia et al. | |
| 2004/0144393 A1 * | 7/2004 | Conklin | A61C 5/90 128/861 |
| 2005/0003318 A1 * | 1/2005 | Choi | A61C 7/08 433/6 |
| 2005/0055118 A1 | 3/2005 | Nikolskiy et al. | |
| 2006/0223022 A1 * | 10/2006 | Solomon | A61C 7/08 433/6 |
| 2006/0237020 A1 * | 10/2006 | Morgan | A63B 71/085 128/862 |
| 2007/0065768 A1 * | 3/2007 | Nadav | A61C 7/08 433/18 |
| 2007/0084472 A1 | 4/2007 | Berghash | |
| 2007/0254256 A1 | 11/2007 | Farrell | |
| 2010/0129763 A1 | 5/2010 | Kuo | |
| 2010/0269836 A1 * | 10/2010 | Roettger | A63B 71/085 433/214 |

FOREIGN PATENT DOCUMENTS

| | | |
|---|---|---|
| AU | 5598894 A | 6/1994 |
| CA | 1121955 A | 4/1982 |
| DE | 2749802 A1 | 5/1978 |
| DE | 69327661 T2 | 7/2000 |
| EP | 0091876 A1 | 10/1983 |
| EP | 0299490 A2 | 1/1989 |
| EP | 0376873 A2 | 7/1990 |
| EP | 0490848 A2 | 6/1992 |
| EP | 0541500 A1 | 5/1993 |
| EP | 0667753 B1 | 1/2000 |
| EP | 0774933 B1 | 12/2000 |
| EP | 0731673 B1 | 5/2001 |
| ES | 463897 A1 | 1/1980 |
| FR | 2369828 A1 | 6/1978 |
| FR | 2652256 A1 | 3/1991 |
| GB | 1550777 A | 8/1979 |
| JP | S5358191 A | 5/1978 |
| JP | H0428359 A | 1/1992 |
| JP | H08508174 A | 9/1996 |
| WO | WO-9008512 A1 | 8/1990 |
| WO | WO-9104713 A1 | 4/1991 |
| WO | WO-9410935 A1 | 5/1994 |
| WO | WO-9832394 A1 | 7/1998 |
| WO | WO-9844865 A1 | 10/1998 |
| WO | WO-9858596 A1 | 12/1998 |
| WO | WO-2008102132 A1 | 8/2008 |
| WO | WO-2009067731 A1 | 6/2009 |

OTHER PUBLICATIONS

Alcaniz, et al, "An Advanced System for the Simulation and Planning of Orthodontic Treatments," Karl Heinz Hohne and Ron Kikinis (eds.), Visualization in Biomedical Computing, 4th Intl. Conf., VBC '96, Hamburg, Germany, Sep. 22-25, 1996, Springer-Verlag, pp. 511-520.

Alexander et al., "The DigiGraph Work Station Part 2 Clinical Management," JCO, pp. 402-407 (Jul. 1990).

Altschuler, "3D Mapping of Maxillo-Facial Prosthesis," AADR Abstract #607, 2 pages total, (1980).

Altschuler et al., "Analysis of 3-D Data for Comparative 3-D Serial Growth Pattern Studies of Oral-Facial Structures," AADR Abstracts, Program and Abstracts of Papers, 57th General Session, IADR HP Annual Session, Mar. 29, 1979-Apr. 1, 1979, New Orleans Marriot, Journal of Dental Research, vol. 58, Jan. 1979, Special Issue A, p. 221.

Altschuler et al., "Laser Electro-Optic System for Rapid Three-Dimensional (3D) Topographic Mapping of Surfaces," Optical Engineering, 20(6):953-961 (1981).

Altschuler et al., "Measuring Surfaces Space-Coded by a Laser-Projected Dot Matrix," SPIE Imaging Applications for Automated Industrial Inspection and Assembly, vol. 182, p. 187-191 (1979).

Andersson et al., "Clinical Results with Titanium Crowns Fabricated with Machine Duplication and Spark Erosion," Acta. Odontol. Scand., 47:279-286 (1989).

Andrews, The Six Keys to Optimal Occlusion Straight Wire, Chapter 3, pp. 13-24 (1989).

Bartels, et al., An Introduction to Splines for Use in Computer Graphics and Geometric Modeling, Morgan Kaufmann Publishers, pp. 422-425 (1987).

Baumrind, "A System for Craniofacial Mapping Through the Integration of Data from Stereo X-Ray Films and Stereo Photographs," an invited paper submitted to the 1975 American Society of Photogram Symposium on Close-Range Photogram Systems, University of Ill., Aug. 26-30, 1975, pp. 142-166.

Baumrind et al., "A Stereophotogrammetric System for the Detection of Prosthesis Loosening in Total Hip Arthroplasty," NATO Symposium on Applications of Human Biostereometrics, Jul. 9-13, 1978, SPIE, vol. 166, pp. 112-123.

Baumrind et al., "Mapping the Skull in 3-D," reprinted from J. Calif. Dent. Assoc., 48(2), 11 pages total, (1972 Fall Issue).

Baumrind, "Integrated Three-Dimensional Craniofacial Mapping: Background, Principles, and Perspectives," Semin. in Orthod., 7(4):223-232 (Dec. 2001).

Begole et al., "A Computer System for the Analysis of Dental Casts," The Angle Orthod., 51(3):253-259 (Jul. 1981).

(56) References Cited

OTHER PUBLICATIONS

Bernard et al.,"Computerized Diagnosis in Orthodontics for Epidemiological Studies: A Progress Report," Abstract, J. Dental Res. Special Issue, vol. 67, p. 169, paper presented at International Association for Dental Research 66th General Session, Mar. 9-13, 1988, Montreal, Canada.
Bhatia et al., "A Computer-Aided Design for Orthognathic Surgery," Br. J. Oral Maxillofac. Surg., 22:237-253 (1984).
Biggerstaff, "Computerized Diagnostic Setups and Simulations," Angle Orthod., 40(1):28-36 (Jan. 1970).
Biggerstaff et al., "Computerized Analysis of Occlusion in the Postcanine Dentition," Am. J. Orthod., 61(3): 245-254 (Mar. 1972).
Biostar Opeation & Training Manual. Great Lakes Orthodontics, Ltd. 199 Fire Tower Drive, Tonawanda, New York. 14150-5890, 20 pages total (1990).
Blu, et al., "Linear interpolation revitalized", IEEE Trans. Image Proc., 13(5):710-719 (May 2004.
Bourke, "Coordinate System Transformation," (Jun. 1996), p. 1, retrieved from the Internet Nov. 5, 2004, URL< http://astronomy.swin.edu.au/—pbourke/prolection/coords>.
Boyd et al., "Three Dimensional Diagnosis and Orthodontic Treatment of Complex Malocclusions With the Invisalipn Appliance," Semin. Orthod., 7(4):274-293 (Dec. 2001).
Brandestini et al., "Computer Machined Ceramic Inlays: In Vitro Marginal Adaptation," J. Dent. Res. Special Issue, Abstract 305, vol. 64, p. 208 (1985).
Brook et al., "An Image Analysis System for the Determination of Tooth Dimensions from Study Casts: Comparison with Manual Measurements of Mesio-distal Diameter," J. Dent. Res., 65(3):428-431 (Mar. 1986).
Burstone et al., Precision Adjustment of the Transpalatal Lingual Arch: Computer Arch Form In Predetermination, Am, Journal of Orthodontics, vol. 79, No. 2 (Feb. 1981), pp. 115-133.
Burstone (interview), "Dr. Charles J. Burstone on The Uses of the Computer in Orthodontic Practice (Part 1)," J. Clin. Orthod., 13(7):442-453 (Jul. 1979).
Burstone (interview), "Dr. Charles J. Burstone on The Uses of the Computer in Orthodontic Practice (Part 2)," J. Clin. Orthod., 13(8):539-551 (Aug. 1979).
Cardinal Industrial Finishes, Powder Coatings information posted at<http://www.cardinalpaint.com> on Aug. 25, 2000, 2 pages.
Carnaghan, "An Alternative to Holograms for the Portrayal of Human Teeth," 4th Int'l. Conf. on Holographic Systems, Components and Applications, Sep. 15, 1993, pp. 228-231.
Chaconas et al., "The DigiGraph Work Station, Part 1, Basic Concepts," JCO, pp. 360-367 (Jun. 1990).
Chafetz et al., "Subsidence of the Femoral Prosthesis, A Stereophotogrammetric Evaluation," Clin. Orthop. Relat. Res., No. 201, pp. 60-67 (Dec. 1985).
Chiappone, (1980). Constructing the Gnathologic Setup and Positioner, J. Clin. Orthod, vol. 14, pp. 121-133.
Cottingham, (1969). Gnathologic Clear Plastic Positioner, Am. J. Orthod, vol. 55, pp. 23-31.
Crawford, "CAD/CAM in the Dental Office: Does It Work?", Canadian Dental Journal, vol. 57, No. 2, pp. 121-123 (Feb. 1991).
Crawford, "Computers in Dentistry: Part 1 CAD/CAM: The Computer Moves Chairside," Part 2 F. Duret—A Man with a Vision, "Part 3 The Computer Gives New Vision—Literally," Part 4 Bytes 'N Bites—The Computer Moves from the Front Desk to the Operatory, Canadian Dental Journal, vol. 54 (9), pp. 661-666 (1988).
Crooks, "CAD/CAM Comes to USC," USC Dentistry, pp. 14-17 (Spring 1990).
Cureton, Correcting Malaligned Mandibular Incisors with Removable Retainers, J. Clin. Orthod, vol. 30, No. 7 (1996) pp. 390-395.
Curry et al., "Integrated Three-Dimensional Craniofacial Mapping at the Craniofacial Research Instrumentation Laboratory/Universify of the Pacific," Semin. Orthod., 7(4):258-265 (Dec. 2001).

Cutting et a/., "Three-Dimensional Computer-Assisted Design of Craniofacial Surgical Procedures: Optimization and Interaction with Cephalometric and CT-Based Models," Plast. 77(6):877-885 (Jun. 1986).
DCS Dental AG, "The CAD/CAM 'DCS Titan System' for Production of Crowns/Bridges," DSC Production AG, pp. 1-7 (Jan. 1992).
Definition for gingiva. Dictionary.com p. 1-3. Retrieved from the internet Nov. 5, 2004< http://reference.com/search/search?q=gingiva>.
Defranco et al., "Three-Dimensional Large Displacement Analysis of Orthodontic Appliances," J. Biomechanics, 9:793-801 (1976).
Dental Institute University of Zurich Switzerland, Program for International Symposium JD on Computer Restorations: State of the Art of the CEREC-Method, May 1991, 2 pages total.
Dentrac Corporation, Dentrac document, pp. 4-13 (1992).
Dent-X posted on Sep. 24, 1998 at< http://www.dent-x.com/DentSim.htm>, 6 pages.
Doyle, "Digital Dentistry," Computer Graphics World, pp. 50-52, 54 (Oct. 2000).
DuraClear™ product information, Allesee Orthodontic Appliances-Pro Lab, 1 page (1997).
Duret et al., "CAD/CAM Imaging in Dentistry," Curr. Opin. Dent., 1:150-154 (1991).
Duret et al, "CAD-CAM in Dentistry," J. Am. Dent. Assoc. 117:715-720 (Nov. 1988).
Duret, "The Dental CAD/CAM, General Description of the Project," Hennson International Product Brochure, 18 pages total, Jan. 1986.
Duret,"Vers Une Prosthese Informatisee," (English translation attached), Tonus, vol. 75, pp. 55-57 (Nov. 15, 1985).
Economides, "The Microcomputer in the Orthodontic Office," JCO, pp. 767-772 (Nov. 1979).
Elsasser, Some Observations on the History and Uses of the Kesling Positioner, Am. J. Orthod. (1950) 36:368-374.
English translation of Japanese Laid-Open Publication No. 63-11148 to inventor T. Ozukuri (Laid-Open on Jan. 18, 1998) pp. 1-7.
Felton et al., "A Computerized Analysis of the Shape and Stability of Mandibular Arch Form," Am. J. Orthod. Dentofacial Orthop., 92(6):478-483 (Dec. 1987).
Friede et al., "Accuracy of Cephalometric Prediction in Orthognathic Surgery," Abstract of Papers, J. Dent. Res., 70:754-760 (1987).
Futterling et a/., "Automated Finite Element Modeling of a Human Mandible with Dental Implants," JS WSCG '98—Conference Program, retrieved from the Internet:< http://wscg.zcu.cz/wscg98/papers98/Strasser 98.pdf>, 8 pages.
Gao et al., "3-D element Generation for Multi-Connected Complex Dental and Mandibular Structure," Proc. Intl Workshop on Medical Imaging and Augmented Reality, pp. 267-271 (Jun. 12, 2001).
Gim-Alldent Deutschland, "Das DUX System: Die Technik," 2 pages total (2002).
Gottleib et al., "JCO Interviews Dr. James A. McNamura, Jr., on the Frankel Appliance: Part 2: Clinical 1-1 Management," J. Clin. Orthod., 16(6):390-407 (Jun. 1982).
Grayson, "New Methods for Three Dimensional Analysis of Craniofacial Deformity, Symposium: JW Computerized Facial Imaging in Oral and Maxiiofacial Surgery," AAOMS, 3 pages total, (Sep. 13, 1990).
Guess et al., "Computer Treatment Estimates In Orthodontics and Orthognathic Surgery," JCO, pp. 262-28 (Apr. 1989).
Heaven et a/., "Computer-Based Image Analysis of Artificial Root Surface Caries," Abstracts of Papers, J. Dent. Res., 70:528 (Apr. 17-21, 1991).
Highbeam Research, "Simulating Stress Put on Jaw," Tooling & Production [online], Nov. 1996, n pp. 1-2, retrieved from the Internet on Nov. 5, 2004, URL http://static.highbeam.com/t/toolingampproduction/november011996/simulatingstressputonfa . . . >.
Hikage, "Integrated Orthodontic Management System for Virtual Three-Dimensional Computer Graphic Simulation and Optical Video Image Database for Diagnosis and Treatment Planning", Journal of Japan KA Orthodontic Society, Feb. 1987, English translation, pp. 1-38, Japanese version, 46(2), pp. 248-269 (60 pages total).

(56) References Cited

OTHER PUBLICATIONS

Hoffmann, et al., "Role of Cephalometry for Planning of Jaw Orthopedics and Jaw Surgery Procedures," (Article Summary in English, article in German), Informatbnen, pp. 375-396 (Mar. 1991).

Hojjatie et al., "Three-Dimensional Finite Element Analysis of Glass-Ceramic Dental Crowns," J. Biomech., 23(11):1157-1166 (1990).

Huckins, "CAD-CAM Generated Mandibular Model Prototype from MRI Data," AAOMS, p. 96 (1999).

Important Tip About Wearing the Red White & Blue Active Clear Retainer System, Allesee Orthodontic Appliances-Pro Lab, 1 page 1998).

JCO Interviews, Craig Andreiko, DDS, MS on the Elan and Orthos Systems, JCO, pp. 459-468 (Aug. 1994).

JCO Interviews, Dr. Homer W. Phillips on Computers in Orthodontic Practice, Part 2, JCO. 1997; 1983:819-831.

Jerrold, "The Problem, Electronic Data Transmission and the Law," AJO-DO, pp. 478-479 (Apr. 1988).

Jones et al., "An Assessment of the Fit of a Parabolic Curve to Pre- and Post-Treatment Dental Arches," Br. J. Orthod., 16:85-93 (1989).

JP Faber et al., "Computerized Interactive Orthodontic Treatment Planning," Am. J. Orthod., 73(1):36-46 (Jan. 1978).

Kamada et.al., Case Reports On Tooth Positioners Using LTV Vinyl Silicone Rubber, J. Nihon University School of Dentistry (1984) 26(1): 11-29.

Kamada et.al., Construction of Tooth Positioners with LTV Vinyl Silicone Rubber and Some Case KJ Reports, J. Nihon University School of Dentistry (1982) 24(1):1-27.

Kanazawa et al., "Three-Dimensional Measurements of the Occlusal Surfaces of Upper Molars in a Dutch Population," J. Dent Res., 63(11):1298-1301 (Nov. 1984).

Kesling, Coordinating the Predetermined Pattern and Tooth Positioner with Conventional Treatment, KN Am. J. Orthod. Oral Surg. (1946) 32:285-293.

Kesling et al., The Philosophy of the Tooth Positioning Appliance, American Journal of Orthodontics and Oral surgery. 1945; 31:297-304.

Kleeman et al., The Speed Positioner, J. Clin. Orthod. (1996) 30:673-680.

Kochanek, "Interpolating Splines with Local Tension, Continuity and Bias Control," Computer Graphics, ri 18(3):33-41 (Jul. 1984). KM Oral Surgery (1945) 31 :297-30.

Kunii et al., "Articulation Simulation for an Intelligent Dental Care System," Displays 15:181-188 (1994).

Kuroda et al., Three-Dimensional Dental Cast Analyzing System Using Laser Scanning, Am. J. Orthod. Dentofac. Orthop. (1996) 110:365-369.

Laurendeau, et al., "A Computer-Vision Technique for the Acquisition and Processing of 3-D Profiles of 7 KR Dental Imprints: An Application in Orthodontics," IEEE Transactions on Medical Imaging, 10(3):453-461 (Sep. 1991.

Leinfelder, et al., "A New Method for Generating Ceramic Restorations: a CAD-CAM System," J. Am. 1-1 Dent. Assoc., 118(6):703-707 (Jun. 1989).

Manetti, et al., "Computer-Aided Cefalometry and New Mechanics in Orthodontics," (Article Summary in English, article in German), Fortschr Kieferorthop. 44, 370-376 (Nr. 5), 1983.

Mccann, "Inside the ADA," J. Amer. Dent. Assoc., 118:286-294 (Mar. 1989).

Mcnamara et al., "Invisible Retainers," J. Cfin. Orthod., pp. 570-578 (Aug. 1985).

Mcnamara et al., Orthodontic and Orthopedic Treatment in the Mixed Dentition, Needham Press, pp. 347-353 (Jan. 1993).

Moermann et al., "Computer Machined Adhesive Porcelain Inlays: Margin Adaptation after Fatigue Stress," IADR Abstract 339, J. Dent. Res., 66(a):763 (1987).

Moles, "Correcting Mild Malalignments—As Easy As One, Two, Three," AOA/Pro Corner, vol. 11, No. 1, 2 pages (2002).

Mormann et al., "Marginale Adaptation von adhasuven Porzellaninlays in vitro," Separatdruck aus: Schweiz. Mschr. Zahnmed. 95: 1118-1129, 1985.

Nahoum, "The Vacuum Formed Dental Contour Appliance," N. Y. State Dent. J., 30(9):385-390 (Nov. 1964).

Nash, "CEREC CAD/CAM Inlays: Aesthetics and Durability in a Single Appointment," Dent. Today, 9(8):20, 22-23 (Oct. 1990).

Nishiyama et al., "A New Construction of Tooth Repositioner by LTV Vinyl Silicone Rubber," J. Nihon Univ. Sch. Dent., 19(2):93-102 (1977).

Paul et al., "Digital Documentation of Individual Human Jaw and Tooth Forms for Applications in Orthodontics, Oral Surgery and Forensic Medicine" Proc. of the 24th Annual Conf. of the IEEE Industrial Electronics Society (IECON '98), Sept. 4, 1998, pp. 2415-2418.

Pinkham, "Foolish Concept Propels Technology," Dentist, 3 pages total, Jan./Feb. 1989.

Pinkham, "Inventor's CAD/CAM May Transform Dentistry," Dentist, 3 pages total, Sep. 1990.

Ponitz, "Invisible Retainers," Am. J. Orthod., 59(3):266-272 (Mar. 1971).

PROCERA Research Projects, "PROCERA Research Projects 1993—Abstract Collection," pp. 3-7; 28 (1993).

Proffit et al., Contemporary Orthodontics, (Second Ed.), Chapter 15, Mosby Inc., pp. 470-533 (Oct. 1993.

Raintree Essix & Ars Materials, Inc., Raintree Essix, Technical Magazine Table of contents and Essix Appliances,< http://www.essix.com/magazine/defaulthtml> Aug. 13, 1997.

Redmond et al., "Clinical Implications of Digital Orthodontics," Am. J. Orthod. Dentofacial Orthop., 117(2):240-242 (2000).

Rekow, "A Review of the Developments in Dental CAD/CAM Systems," (contains references to Japanese efforts and content of the papers of particular interest to the clinician are indicated with a one line summary of their content in the bibliography), Curr. Opin. Dent., 2:25-33 (Jun. 1992).

Rekow, "CAD/CAM in Dentistry: A Historical Perspective and View of the Future," J. Can. Dent. Assoc., 58(4):283, 287-288 (Apr. 1992).

Rekow, "Computer-Aided Design and Manufacturing in Dentistry: A Review of the State of the Art," J. Prosthet. Dent., 58(4):512-516 (Oct. 1987).

Rekow, "Dental CAD-CAM Systems: What is the State of the Art?", J. Amer. Dent. Assoc., 122:43-48 1991.

Rekow et a/., "CAD/CAM for Dental Restorations—Some of the Curious Challenges," IEEE Trans. Biomed. Eng., 38(4):344-345 (Apr. 1991.

Rekow et al., "CAD/CAM for Dental Restorations—Some of the Curious Challenges," IEEE Trans. Biomed. Eng., 38(4):314-318 (Apr. 1991).

Rekow et al., "Comparison of Three Data Acquisition Techniques for 3-D Tooth Surface Mapping," Annual International Conference of the IEEE Engineering in Medicine and Biology Society, 13(1):344-345 1991.

Rekow, "Feasibility of an Automated System for Production of Dental Restorations, Ph.D. Thesis," Univ. of Minnesota, 244 pages total, Nov. 1988.

Richmond et al., "The Development of a 3D Cast Analysis System," Br. J. Orthod., 13(1):53-54 (Jan. 1986).

Richmond et al., "The Development of the PAR Index (Peer Assessment Rating): Reliability and Validity," Eur. J. Orthod., 14:125-139 (1992).

Richmond, "Recording The Dental Cast In Three Dimensions," Am. J. Orthod. Dentofacial Orthop., 92(3):199-206 (Sep. 1987).

Rudge, "Dental Arch Analysis: Arch Form, A Review of the Literature," Eur. J. Orthod., 3(4):279-284 1981.

Sakuda et al., "Integrated Information-Processing System In Clinical Orthodontics: An Approach with Use of a Computer Network System," Am. J. Orthod. Dentofacial Orthop., 101(3): 210-220 (Mar. 1992).

Schellhas et al., "Three-Dimensional Computed Tomography in Maxillofacial Surgical Planning," Arch. Otolampl. Head Neck Sur9., 114:438-442 (Apr. 1988).

(56) References Cited

OTHER PUBLICATIONS

Schroeder et al., Eds. The Visual Toolkit, Prentice Hall PTR, New Jersey (1998) Chapters 6, 8 & 9, (pp. 153-210,309-354, and 355-428, respectively.
Shilliday, (1971). Minimizing finishing problems with the minipositioner, Am. J. Orthod. 59:596-599.
Shore hardness ISO 868. Accessed Feb. 22, 2011. http://www.ides.com/property_descriptions/ISO868.asp.
Siemens, "CEREC—Computer-Reconstruction," High Tech in der Zahnmedizin, 14 pages total (2004).
Sinclair, "The Readers' Corner," J. Clin. Orthod., 26(6):369-372 (Jun. 1992).
Sirona Dental Systems GmbH, CEREC 3D, Manuel utiiisateur, Version 2.0X (in French), 2003,114 pages total.
Stoll et al., "Computer-aided Technologies in Dentistry," (article summary in English, article in German), Dtsch Zahna'rztl Z 45, pp. 314-322 (1990).
Sturman, "Interactive Keyframe Animation of 3-D Articulated Models," Proceedings Graphics Interface '84, May-Jun. 1984, pp. 35-40.
The Choice Is Clear: Red, White & Blue . . . The Simple, Affordable, No-Braces Treatment, Allesee HI Orthodontic Appliances-Pro Lab product information for doctors. http://ormco.com/aoa/appliancesservices/RWB/doctorhtml>, 5 pages (May 19, 2003).
The Choice is Clear: Red, White & Blue . . . The Simple, Affordable, No-Braces Treatment, Allesee HJ Orthodontic Appliances-Pro Lab product information for patients,< http://ormco.com/aoa/appliancesservices/RWB/patients.html>, 2 pages (May 19, 2003).
The Choice Is Clear: Red, White & Blue . . . The Simple, Affordable, No-Braces Treatment, Allesee Orthodontic Appliances-Pro Lab product information, 6 pages (2003).
The Red, White & Blue Way to Improve Your Smile! Allesee Orthodontic Appliances-Pro Lab product information for patients, 2 pages 1992.
Truax L., "Truax Clasp-Less(TM) Appliance System," Funct. Orthod., 9(5):22-4, 26-8 (Sep.-Oct. 1992).
Tru-Tain Orthodontic & Dental Supplies, Product Brochure, Rochester, Minnesota 55902, 16 pages total (1996).
U.S. Department of Commerce, National Technical Information Service, "Automated Crown Replication Using Solid Photography SM," Solid Photography Inc., Melville NY, Oct. 1977, 20 pages total.
U.S. Department of Commerce, National Technical Information Service, "Holodontography: An Introduction to Dental Laser Holography," School of Aerospace Medicine Brooks AFB Tex, Mar. 1973, 37 pages total.
U.S. Appl. No. 60/050,342, filed Jun. 20, 1997, 41 pages total.
Van Der Linden, "A New Method to Determine Tooth Positions and Dental Arch Dimensions," J. Dent. Res., 51(4):1104 (Jul.-Aug. 1972).
Van Der Linden et al., "Three-Dimensional Analysis of Dental Casts by Means of the Optocom," J. Dent. Res., p. 1100 (Jul.-Aug. 1972).
Van Der Zel, "Ceramic-Fused-to-Metal Restorations with a New CAD/CAM System," Quintessence Int., 24(11)769-778 (1993.
Varady et al., "Reverse Engineering Of Geometric Models—An Introduction," Computer-Aided Design, 29(4):255-268,1997.
Verstreken et al., "An Image-Guided Planning System for Endosseous Oral Implants," IEEE Trans. Med. Imaging, 17(5):842-852 (Oct. 1998).
Warunek et al., Physical and Mechanical Properties of Elastomers in Orthodonic Positioners, Am J. Orthod. Dentofac. Orthop, vol. 95, No. 5, (May 1989) pp. 399-400.
Warunek et.al., Clinical Use of Silicone Elastomer Applicances, JCO (1989) XXIII(10):694-700.
Wells, Application of the Positioner Appliance in Orthodontic Treatment, Am. J. Orthodont. (1970) 58:351-366.
Williams, "Dentistry and CAD/CAM: Another French Revolution," J. Dent. Practice Admin., pp. 2-5 (Jan./Mar. 1987).
Williams, "The Switzerland and Minnesota Developments in CAD/CAM," J. Dent. Practice Admin., pp. 50-55 (Apr./Jun. 1987).
Wishan, "New Advances in Personal Computer Applications for Cephalometric Analysis, Growth Prediction, Surgical Treatment Planning and Imaging Processing," Symposium: Computerized Facial Imaging in Oral and Maxiiofacial Surgery Presented on Sep. 13, 1990.
WSCG'98—Conference Program, "The Sixth International Conference in Central Europe on Computer Graphics and Visualization '98," Feb. 9-13, 1998, pp. 1-7, retrieved from the Internet on Nov. 5, 2004, URL<http://wscg.zcu.cz/wscg98/wscg98.h>.
Xia et al., "Three-Dimensional Virtual-Reality Surgical Planning and Soft-Tissue Prediction for Orthognathic Surgery," IEEE Trans. Inf. Technol. Biomed., 5(2):97-107 (Jun. 2001).
Yamamoto et al., "Optical Measurement of Dental Cast Profile and Application to Analysis of Three-Dimensional Tooth Movement in Orthodontics," Front. Med. Biol. Eng., 1(2):119-130 (1988).
Yamamoto et al., "Three-Dimensional Measurement of Dental Cast Profiles and Its Applications to Orthodontics," Conf. Proc. IEEE Eng. Med. Biol. Soc., 12(5):2051-2053 (1990).
Yamany et al., "A System for Human Jaw Modeling Using Intra-Oral Images," Proc. of the 20th Annual Conf. of the IEEE Engineering in Medicine and Biology Society, Nov. 1, 1998, vol. 2, pp. 563-566.
Yoshii, "Research on a New Orthodontic Appliance: The Dynamic Positioner (D.P.); I. The D.P. Concept and Implementation of Transparent Silicone Resin (Orthocon)," Nippon Dental Review, 452:61-74 (Jun. 1980).
Yoshii, "Research on a New Orthodontic Appliance: The Dynamic Positioner (D.P.); II. The D.P. Manufacturing Procedure and Clinical Applications," Nippon Dental Review, 454:107-130 (Aug. 1980).
Yoshii, "Research on a New Orthodontic Appliance: The Dynamic Positioner (D.P.); III. The General Concept of the D.P. Method and Its Therapeutic Effect, Part 1, Dental and Functional Reversed Occlusion Case Reports," Nippon Dental Review, 457:146-164 (Nov. 1980).
Yoshii, "Research on a New Orthodontic Appliance: The Dynamic Positioner (D.P.); III.—The General Concept of the D.P. Method and Its Therapeutic Effect, Part 2. Skeletal Reversed Occlusion Case Reports," Nippon Dental Review, 458:112-129 (Dec. 1980).
You May Be A Candidate For This Invisible No-Braces Treatment, Allesee Orthodontic Appliances—Pro Lab product information for patients, 2 pages (2002).

* cited by examiner

SEQUENTIAL MOUTH GUARD

CROSS-REFERENCE

This application is a divisional application of Ser. No. 12/277,191, filed Nov. 24, 2008, which is incorporated herein by reference in its entirety, and to which application we claim priority under 35 USC § 121.

BACKGROUND

The present invention relates generally to the field of orthodontics, and more particularly to dental positioning appliances and mouth guards that provide protection against impact-induced injuries during a course of orthodontic treatment, as well as related methods and systems.

An objective of orthodontics is to move a patient's teeth to positions where function and/or aesthetics are optimized. Traditionally, appliances such as braces are applied to a patient's teeth by a treating practitioner and the set of braces exerts continual force on the teeth and gradually urges them toward their intended positions. Over time and with a series of clinical visits and adjustments to the braces, the practitioner adjusts the appliances to move the teeth toward their final destination.

More recently, alternatives to conventional orthodontic treatment with traditional affixed appliances (e.g., braces) have become available. For example, systems including a series of preformed appliances/aligners have become commercially available from Align Technology, Inc., Santa Clara, Calif., under the tradename Invisalign® System. The Invisalign® System is described in numerous patents and patent applications assigned to Align Technology, Inc. including, for example in U.S. Pat. Nos. 6,450,807, and 5,975,893, as well as on the company's website, which is accessible on the World Wide Web (see, e.g., the url "www.invisalign.com"). The Invisalign® System includes designing and/or fabricating multiple, and sometimes all, of the aligners to be worn by the patient before the aligners are administered to the patient and used to reposition the teeth (e.g., at the outset of treatment). Often, designing and planning a customized treatment for a patient makes use of computer-based 3-dimensional planning/design tools, such as Treat™ from Align Technology, Inc. The design of the aligners can rely on computer modeling of a series of planned successive tooth arrangements, and the individual aligners are designed to be worn over the teeth and elastically reposition the teeth to each of the planned tooth arrangements.

While recently developed orthodontic treatment technologies, such as those described above, represent a considerable advancement in the field of orthodontics, additional advancements remain of interest. For example, certain individuals may engage in a sporting activity during their orthodontic treatment. In many sports, especially in contact sports such as football, a player typically wears a mouth guard so as to protect the player against impact-induced injuries, including concussion. As such, there is a need for innovative products that provide an orthodontic patient with protection against impact-induced injuries.

BRIEF SUMMARY

The present disclosure provides protective positioning appliances, accommodating mouth guards, and covering guards that provide an orthodontic patient with protection against impact-induced injuries, and related systems and methods. The disclosed protective appliances, accommodating mouth guards, and covering guards provide the ability to have a patient's teeth protected while undergoing orthodontic treatment, such with the Invisalign® System. Mouth guards are often used by players of contact sports, such as football.

For a fuller understanding of the nature and advantages of the present invention, reference should be made to the ensuing detailed description and accompanying drawings. Other aspects, objects and advantages of the invention will be apparent from the drawings and detailed description that follows.

DETAILED DESCRIPTION

Protective repositioning appliances, accommodating mouth guards, covering guards and accommodating covering guards are provided that protect an orthodontic patient against impact-induced injuries, as well as related systems and methods. In the absence of adequate protection, players of certain contact sports, such as football, may be exposed to a significant risk of impact-induced injuries. The presently disclosed appliances, guards, systems and methods provide a means by which an orthodontic patient can be protected against oral-related impact induced injuries during a course of orthodontic treatment.

A protective repositioning appliance can be configured to reposition a patient's teeth while protecting the patient against impact-induced injuries. Such a protective repositioning appliance can include teeth receiving cavities that are shaped to resiliently reposition a patient's teeth from a first arrangement towards a second arrangement. A protective repositioning appliance can be further configured to have a shape or material selected to provide protection against impact-induced injury.

An accommodating mouth guard can be configured to protect an orthodontic patient's teeth during a portion of a course of orthodontic treatment, during which the patient's teeth are repositioned from a first arrangement towards a second arrangement. An accommodating mouth guard can include teeth receiving cavities that are shaped to accommodate a range of positions of the patient's teeth. A system of accommodating mouth guards can be used to provide protection during multiple stages of orthodontic treatment, where during each stage a patient's teeth are repositioned by some amount.

A covering guard can be configured to couple with at least a portion of a tooth repositioning appliance. The combination of the covering guard and the tooth repositioning appliance can serve to protect the orthodontic patient against impact-induced injuries. An accommodating covering guard can be configured to couple with a sequence of tooth repositioning appliances.

Tooth Repositioning Appliances

Figure 1:
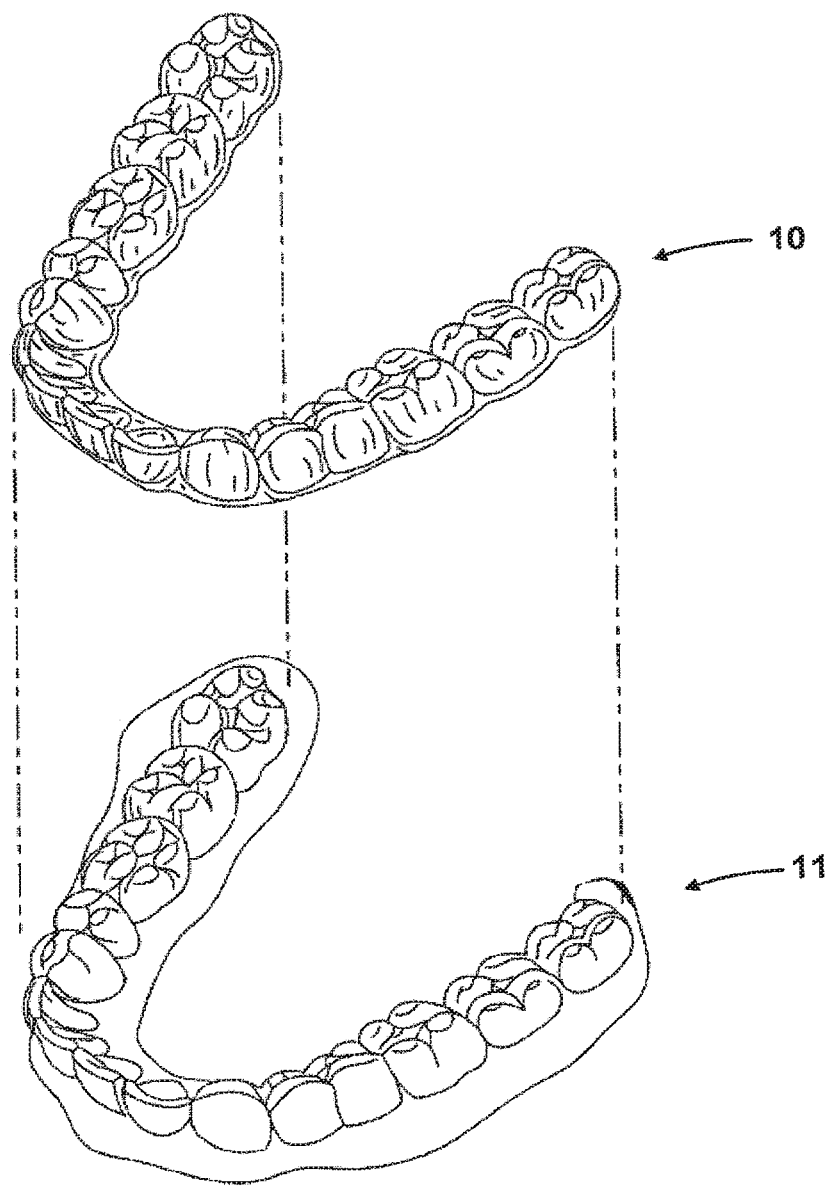
FIG. 1 illustrates a jaw together with an incremental positioning appliance.

FIG. 1 provides an appropriate starting point in a discussion of the present invention with respect to tooth repositioning appliances designed to apply repositioning forces to teeth. A tooth repositioning appliance 10 can be worn by a patient in order to achieve an incremental repositioning of individual teeth in the jaw 11. The appliance can include a shell (e.g., polymeric shell) having teeth-receiving cavities that receive and resiliently reposition the teeth. In one embodiment, a polymeric appliance can be formed from a known thin sheet of suitable elastomeric polymeric material, such a 0.03 inch thermal forming dental material by Tru-Tain Plastics, Rochester, Minn. An appliance can fit over all teeth present in an upper or lower jaw, or less than all of the teeth. In some cases, only certain teeth received by an appliance will be repositioned by the appliance while other teeth can provide a base or anchor region for holding the appliance in place as it applies force against the tooth or teeth targeted for repositioning. In some cases, many or most, and even all, of the teeth will be repositioned at some point during treatment. Teeth that are moved can also serve as a base or anchor for holding the appliance as it is worn by the patient. Typically, no wires or other means will be provided for holding an appliance in place over the teeth. In some cases, however, it may be desirable or necessary to provide individual anchors on teeth with corresponding receptacles or apertures in the appliance so that the appliance can apply a selected force on the tooth. Exemplary appliances, including those utilized in the Invisalign® System, are described in numerous patents and patent applications assigned to Align Technology, Inc. including, for example in U.S. Pat. Nos. 6,450,807, and 5,975,893, as well as on the company's website, which is accessible on the World Wide Web (see, e.g., the url "www.invisalign.com").

An appliance can be designed and/or provided as part of a set or plurality of appliances. In such an embodiment, each appliance may be configured so a tooth-receiving cavity has a geometry corresponding to an intermediate or final tooth arrangement intended for the appliance. The patient's teeth can be progressively repositioned from an initial tooth arrangement to a target tooth arrangement by placing a series of incremental position adjustment appliances over the patient's teeth. A target tooth arrangement can be a planned final tooth arrangement selected for the patient's teeth at the end of all planned orthodontic treatment. Alternatively, a target arrangement can be one of many intermediate arrangements for the patient's teeth during the course of orthodontic treatment, which may include where surgery is recommended, where inter-proximal reduction (IPR) is appropriate, where a progress check is scheduled, where anchor placement is best, where palatal expansion is desirable, etc. As such, it is understood that a target tooth arrangement can be any planned resulting arrangement for the patient's teeth that follows one or more incremental repositioning stages. Likewise, an initial tooth arrangement can be any initial arrangement for the patient's teeth that is followed by one or more incremental repositioning stages. The adjustment appliances can be generated all at the same stage or in sets or batches, e.g., at the beginning of a stage of the treatment, and the patient wears each appliance until the pressure of each appliance on the teeth can no longer be felt or has resulted in the maximum amount of expressed tooth movement for that given stage. A plurality of different appliances (e.g., set) can be designed and even fabricated prior to the patient wearing any appliance of the plurality. After wearing an appliance for an appropriate period of time, the patient replaces the current appliance with the next appliance in the series until no more appliances remain. The appliances are generally not affixed to the teeth and the patient may place and replace the appliances at any time during the procedure (e.g., patient-removable appliances). The final appliance or several appliances in the series may have a geometry or geometries selected to overcorrect the tooth arrangement, i.e., have a geometry which would (if fully achieved) move individual teeth beyond the tooth arrangement which has been selected as the "final." Such over-correction may be desirable in order to offset potential relapse after the repositioning method has been terminated, i.e., to permit movement of individual teeth back toward their pre-corrected positions. Over-correction may also be beneficial to speed the rate of correction, i.e., by having an appliance with a geometry that is positioned beyond a desired intermediate or final position, the individual teeth will be shifted toward the position at a greater rate. In such cases, the use of an appliance can be terminated before the teeth reach the positions defined by the appliance.

Protective Repositioning Appliances

Protective dental appliances are provided that reposition a patient's teeth and provide protection against impact-induced injuries. A protective appliance can include teeth receiving cavities shaped to receive and reposition a patient's teeth. A protective appliance can have a shape or material selected to provide protection against impact-induced injury.

Figure 2:
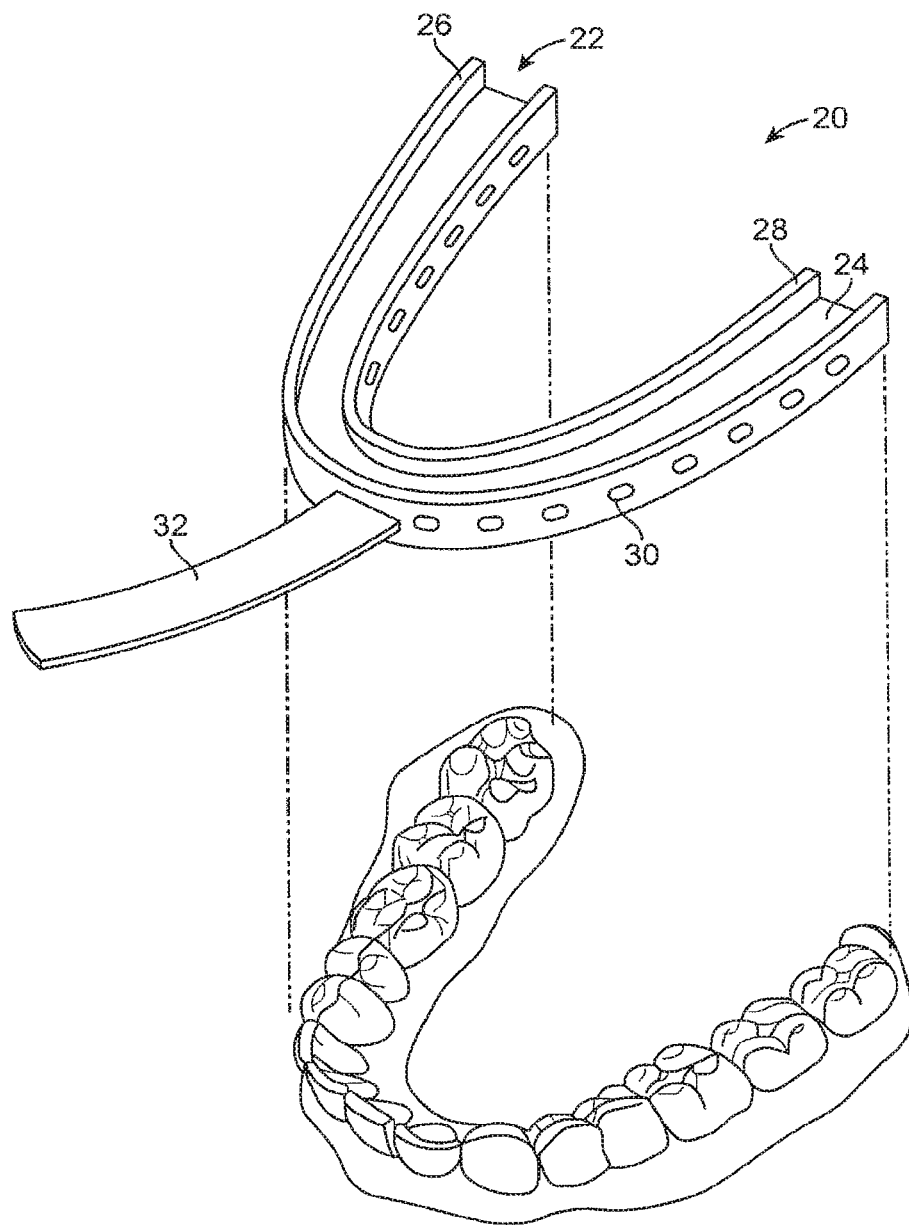
FIG. 2 illustrates a jaw together with a protective incremental positioning appliance according to an embodiment of the present invention.

Referring now to FIG. 2, an embodiment of a protective repositioning appliance 20 is shown. Similar to the tooth repositioning appliance 10 shown in FIG. 1, the protective repositioning appliance 20 includes teeth receiving cavities (hidden from view in FIG. 2) shaped to receive and resiliently reposition a patient's teeth. In the embodiment shown, the protective appliance 20 includes an optional u-shaped tray 22 for receiving the patient's opposite jaw teeth when the patient bites down. The u-shaped tray 22 can be defined in part by an occlusal-pad portion 24, which can be configured so as to exhibit an impact-absorbing compliance during an impact that forces the lower teeth into the upper teeth. The amount of compliance can be influenced by the elasticity and thickness of material used in the occlusal-pad portion. The amount of compliance can also be influenced by the span coverage of the occlusal-pad portion. Additionally, the optional u-shaped tray is partially defined by buccal wall 26 and lingual wall 28. The buccal wall 26 and lingual wall 28 can serve to laterally couple a plurality of a patient's upper and lower jaw teeth so as to help protect against lateral impact-induced injuries by distributing localized lateral impacts to surrounding tissues.

A protective repositioning appliance 20 can come in a range of variations. For example, an appliance 20 can also be adapted to permit better air flow and breathing while the patient bites down. In the embodiment shown, a plurality of traverse air passages 30 are provided so as to permit the flow of air between buccal and lingual sides of the appliance 20. A variety of other configurations can also be used to facilitate mouth breathing. For example, one or more regions of the buccal wall 26, the lingual wall 28, and/or the occlusal-pad portion 24 can be modified so as to provide air passages across the appliance 20. A protective repositioning appliance 20 can also include provisions for the attachment of a connecting leash, such as the leash tab 32 shown. A connecting leash can be used to couple the appliance with the patient so that it will not get misplaced, such as by attaching the connecting leash to a football helmet or the like. A variety of other configurations may be used to provide for the attachment of a connecting leash, such as loops, sockets, or the like.

An appliance can also include a selected color or ornamental design. For example, an appliance can include embedded colors and/or logos, such as for a team or a sponsor. As another example, an appliance can be made with camouflage color for military use. An appliance can also be labeled with personal information, such as the name of the owner, or the number of the owner's athletic jersey.

An appliance can be multi-laminate in composition, such that the different layers of the appliance confer different physical properties. For example, an outer layer can be softer for greater impact protection and an inner layer can be made of harder material for better adaptation to the teeth. An appliance can be tri-laminate, with an outer layer being hard for durability, a middle layer being softer for impact absorption, and an inner layer being hard for better adaptation and retention.

Figure 3:
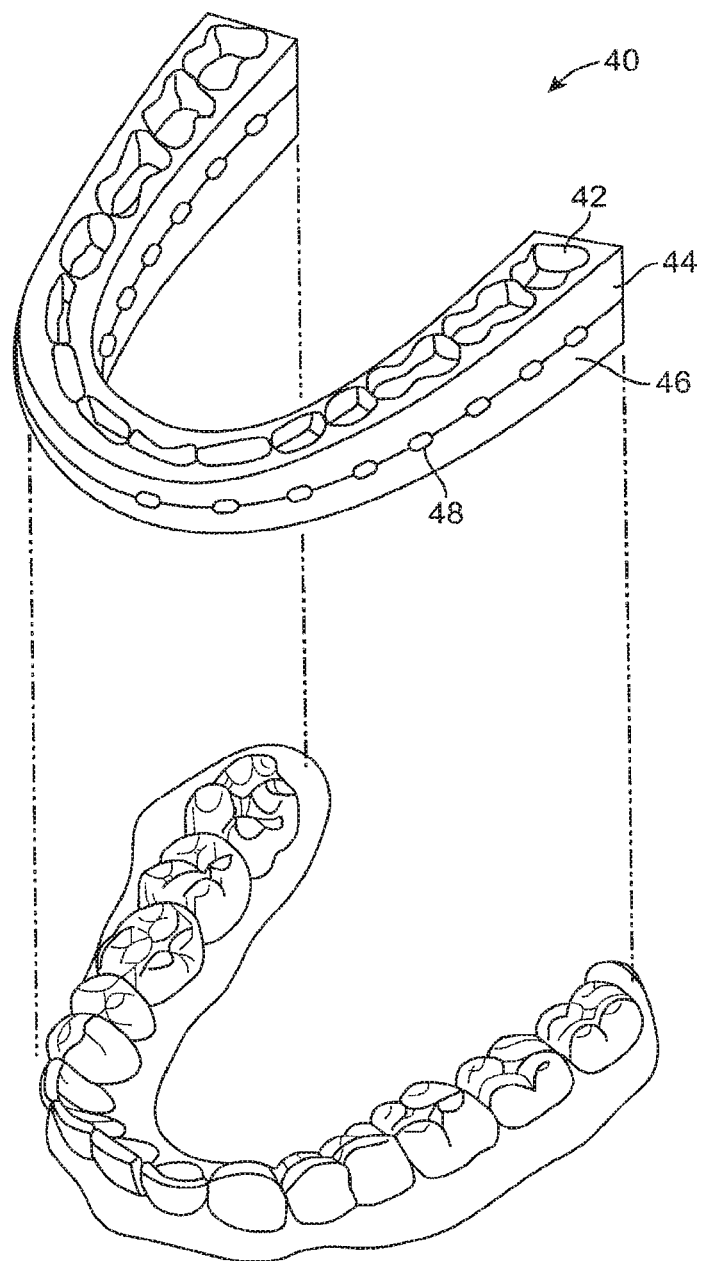
FIG. 3 illustrates a jaw together with a protective incremental positioning appliance according to another embodiment of the present invention.

FIG. 3 illustrates another protective repositioning appliance 40, in accordance with an embodiment. Appliance 40 includes a plurality of teeth receiving cavities 42 for the patient's upper and lower teeth. Appliance 40 can be configured to be an integral unit, or can be configured to include an upper component 44 and a lower component 46, each of which can include teeth receiving cavities 42. Where separate upper and lower components are used, they can be configured with complementary interfacing surfaces (not shown in FIG. 3). These complementary interfacing surfaces can serve to laterally couple a plurality of a patient's upper and lower teeth, thereby helping to distribute localized lateral impacts to surrounding tissues. These complementary surfaces can also provide for snap-fit coupling between the upper component 44 and the lower component 46. Appliance 40 can also be adapted to facilitate mouth breathing while the patient is biting down, such as by the traverse air passages 48 shown. Additionally, an appliance 40 can be adapted to facilitate mouth breathing in a variety of different ways, such as discussed above with reference to FIG. 2.

Figure 4A:
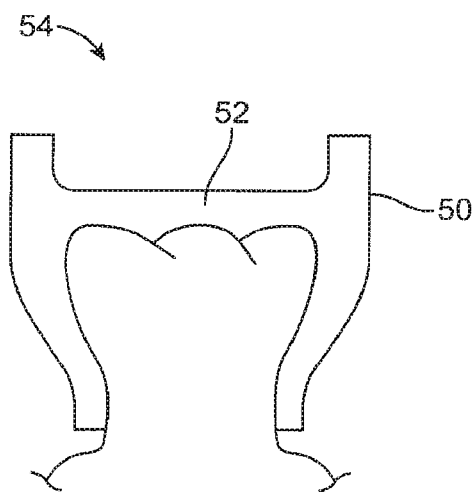
FIGS. 4A and 4B are cross-sectional illustrations of teeth received within protective incremental positioning appliances according to embodiments of the present invention.
Figure 4B:
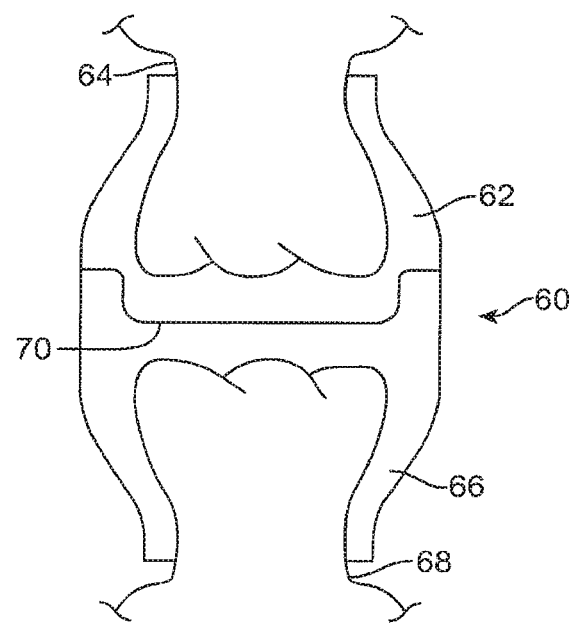

FIGS. 4A and 4B are cross-sectional illustrations of embodiments of protective repositioning appliances. FIG. 4A illustrates a cross-section of an appliance 50 having lower-teeth receiving cavities. The appliance can include an occlusal-pad portion 52 and an optional u-shaped tray 54 for receiving the patient's upper teeth. As discussed above with reference to FIG. 2, the occlusal-pad portion 52 can be configured to exhibit an impact absorbing compliance so as to reduce peak forces transmitted between the patient's jaws during an impact that forces the lower teeth into the upper teeth, or vice-versa. The optional u-shaped tray 54 can be configured to provide coupling between a plurality of the patient's upper and lower teeth, so as to distribute localized lateral impact forces to surrounding tissues thereby reducing the level of localized impact forces felt by local tissues. The appliance 50 of FIG. 4A can be used to protect a patient against impact-induced injuries while simultaneously subjecting the patient's lower teeth to resilient repositioning forces. An analogous, but opposite, appliance can be used for to reposition the patient's upper teeth while providing protection against impact-induced injuries. The appliance 60 of FIG. 4B includes an upper component 62 having teeth receiving cavities for the patient's upper teeth 64, and a lower component 66 having teeth receiving cavities for the patient's lower teeth 68.

Figure 5:
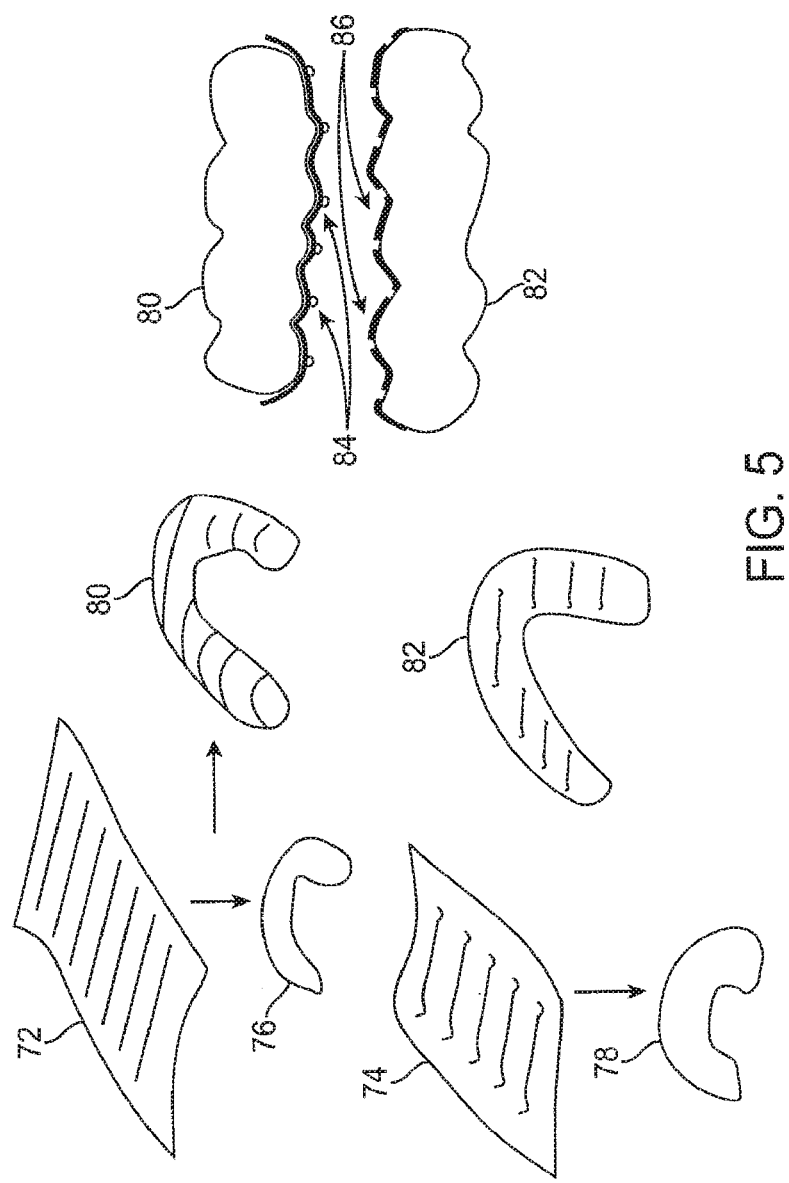
FIG. 5 illustrates a fabrication process that can be used to create upper arch and lower arch protective incremental positioning appliances, accommodating mouth guards, covering guards, and/or accommodating covering guards that have complementary coupling features according to embodiments of the present invention.

The upper and lower components can be configured with complementary shaped interfacing surfaces, such as the snap-fit surfaces 70 shown. These complementary-shaped surfaces can provide for lateral coupling between a plurality of the patient's upper and lower teeth, thereby enhancing the distribution of localized lateral impact forces to surrounding tissues. Various complementary shaped interfacing surfaces can be used. For example, FIG. 5 illustrates a fabrication process that can be used to create upper arch and lower arch protective incremental positioning appliances, accommodating mouth guards, covering guards, and/or accommodating covering guards that have complementary coupling features. Thin sheets 72, 74 of a suitable elastomeric polymeric material can be configured with complementary coupling features, such as ribs on sheet 72 and grooves on sheet 74, or any other complementary shaped features. Sheet 72 can be formed over a positive mold 76 to form an upper arch component 80 having complementary shaped features disposed on its outer surface. Likewise, sheet 74 can be formed over a positive mold 78 to form a lower arch component 82 having complementary shaped features disposed on its outer surface. When worn by a patient, one or more upper arch component features 84 can interface with one or more lower arch component features 86 so as to provide the above discussed lateral coupling. Components 80, 82 can be a protective incremental positioning appliance, an accommodating mouth guard, a covering guard, or an accommodating covering guard.

Accommodating Mouth Guards

Accommodating mouth guards are provided that can be used during a portion of a course of orthodontic treatment. An accommodating mouth guard can accommodate a range of positions of the patient's teeth. An accommodating mouth guard may or may not supply any repositioning forces to a patient's teeth. Instead, an accommodating mouth guard can be used in place of a tooth positioning appliance during a sporting activity.

Accommodating mouth guards are provided that can be used during a course of orthodontic treatment. An accommodating mouth guard can include teeth receiving cavities shaped to accommodate a patient's teeth in a first and a second arrangement. An accommodating mouth guard can have a shape or material selected to provide protection against impact-induced injury.

Figure 6A:
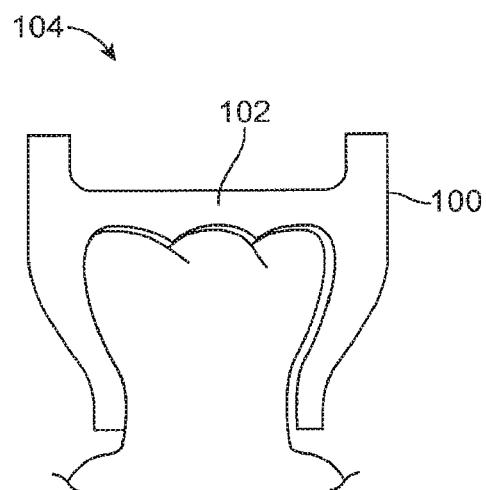
FIGS. 6A and 6B are cross-sectional illustrations of teeth received within accommodating mouth guards according to embodiments of the present invention.
Figure 6B:
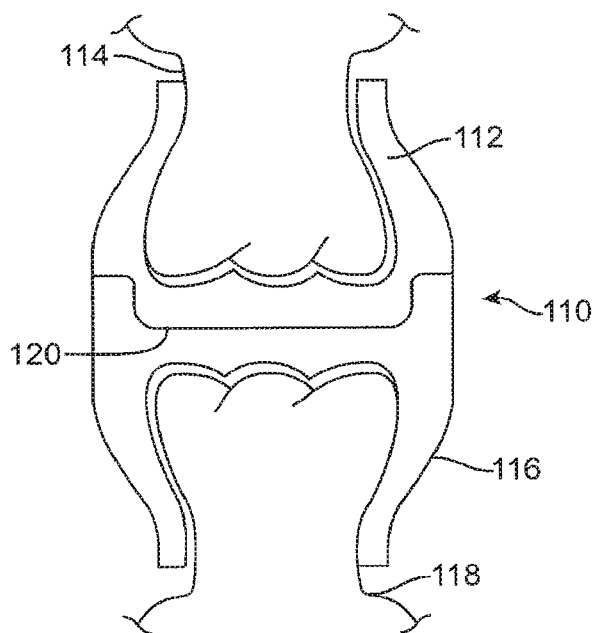

FIGS. 6A and 6B are cross-sectional illustrations of embodiments of accommodating mouth guards. FIG. 6A illustrates a cross-section of an accommodating mouth guard 100 having lower-teeth receiving cavities. Accommodation of a range of positions of the patient's teeth can be provided in a number of ways. For example, as shown in FIG. 6A, the teeth receiving cavities can be configured with additional volume selected to accommodate the range of positions. This additional volume provides a cavity of sufficient dimensions to accommodate a tooth in any of the range of positions along the path of possible tooth positions from the initial point to the end point (i.e., the tooth's swept volume). As another example, the appliance cavity walls can include sufficient compliance so as to be able to deflect a sufficient amount to accept the tooth in any of the range of positions. A combination of additional volume and cavity wall compliance can also be used. As such, it is understood that a tooth receiving cavity can be shaped to accommodate a range of positions for the tooth in a variety of ways, including those discussed above. Additionally, an accommodating mouth guard can include features similar to features of a protective repositioning appliance, such as the occlusal-pad portion 102 and the optional u-shaped tray 104 as shown, and as discussed above with reference to FIG. 4A. Similarly, the accommodating mouth guard 100 of FIG. 6A can be likewise configured for a patient's upper teeth.

Accommodating mouth guards can also be advantageously configured to selectively provide accommodation only for teeth that are being repositioned during a stage of orthodontic treatment. During orthodontic treatment using repositioning appliances, an appliance, or even a series of appliances, may be used to reposition a subset of the patient's teeth. The remaining teeth may not be repositioned during the stage of treatment. The teeth receiving cavities for non-repositioned teeth can be configured without accommodation, thereby providing for a more secure coupling with the non-moving teeth. This more secure coupling can provide for a more secure coupling between the accommodating mouth guard and the patient's teeth in general.

The accommodating mouth guard 110 of FIG. 6B includes an upper component 112 having teeth receiving cavities for the patient's upper teeth 114, and a lower component 116 having teeth receiving cavities for the patient's lower teeth 118. As discussed above with reference to FIG. 6A, these teeth receiving cavities can be configured to accommodate a range of positions for any subset of teeth that are being repositioned during a stage of orthodontic treatment, and omit accommodation for any subset of teeth that are not being repositioned during the stage of treatment. Similarly, the upper and lower component can be configured with complementary-shaped interfacing surfaces, such as the snap-fit surfaces 120 shown. These complementary-shaped surfaces can provide for a level of lateral coupling between a plurality of the patient's upper and lower teeth, thereby enhancing the distribution of localized lateral impact forces to surrounding tissues.

Figure 7:
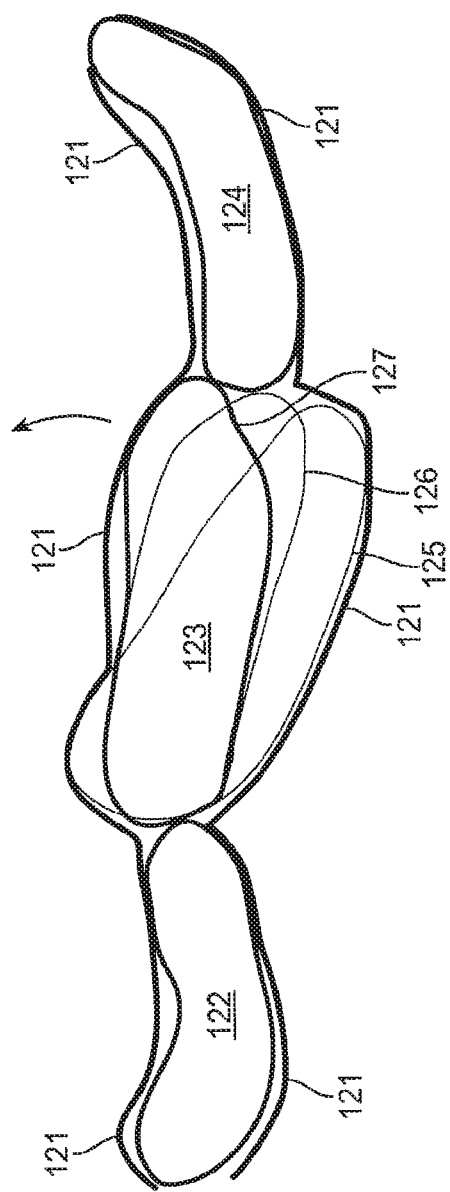
FIG. 7 is a cross-sectional diagram illustrating the accommodation of a single tooth along a path of intermediate stages according to embodiments of the present invention.

FIG. 7 is a simplified cross-sectional diagram of the cavity walls 121 of an accommodating mouth guard and received teeth 122, 123, 124 that illustrates the accommodation of a single tooth 123 along a path of movement. As can be seen, the cavity walls 121 that surround tooth 123 are configured to accommodate the entire path of the tooth 123 (i.e., the swept volume) for a sequence of positions 125, 126, 127. Such accommodation can also be incorporated into an accommodating covering guard.

Accommodating mouth guards may also be designed to accommodate orthodontic treatment that is being performed using fixed wire and bracket braces. The accommodation in the mouth guard would allow the mouth guard to fit around both the braces and the archwire, and enable a range of tooth movements to take place for the given time period for which the guard is applicable. The braces treatment plan can be digitally planned out in advance, so that an accommodating mouth guard can be designed to work for a specific portion of the treatment plan.

Covering Guards

Covering guards are provided that can be coupled with a tooth repositioning appliance so as to provide protection against impact-induced injuries. A covering guard can include a guard segment that covers at least a portion of an appliance. The combination of a guard segment and an appliance can have a shape or material selected to provide protection against impact-induced injury.

Figure 8A:
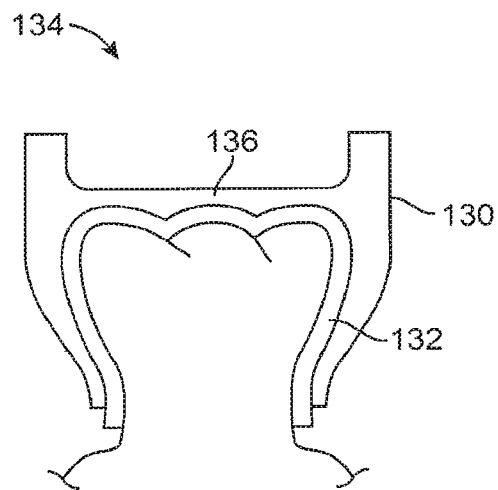
FIGS. 8A and 8B are cross-sectional illustrations of teeth received within incremental positioning appliances that are coupled with covering guards in accordance with embodiments of the present invention.

Covering guards are provided that can be used in combination with a repositioning appliance so as to provide protection against impact-induced injury. FIG. 8A is a cross-sectional illustration of a covering guard 130 in accordance with an embodiment. As shown, a covering guard can be coupled with a basic repositioning appliance 132. A covering guard can be coupled with a repositioning appliance 132 in a variety of ways. For example, the covering guard 130 shown includes repositioning appliance receiving cavities that provide an interface with the underlying repositioning appliance 132. A covering guard can include a variety of features similar to features discussed above, such as an optional u-shaped tray 134 for receiving teeth from the opposing arch, and an occlusal-pad portion 136. As discussed above, the optional u-shaped tray 134 can provide for lateral coupling between a plurality of the patient's upper and lower teeth, thereby helping to distribute localized lateral impact forces to surrounding tissues. The occlusal-pad portion 136 can be configured to provide an impact-absorbing compliance so as to reduce peak forces transmitted between the patient's arches during an impact that forces the arches together. This reduction of peak transmitted forces can help to reduce the occurrence of impact-induced injuries, such as damage to teeth or concussion.

Figure 8B:
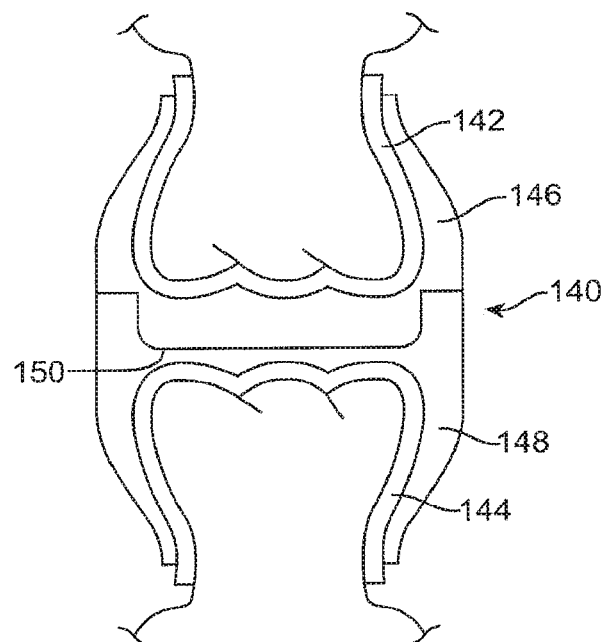

FIG. 8B is a cross-sectional illustration of a covering guard 140 in accordance with an embodiment. The covering guard 140 includes an upper component 146 adapted to couple with an upper-arch appliance 142, and a lower component 148 adapted to couple with a lower-arch appliance 144. As discussed above, a variety of ways can be used to couple the upper and lower components with an underlying repositioning appliance. In the embodiment shown, the upper and lower components have appliance receiving cavities that provide an interface with the underlying repositioning appliance. The upper and lower component can be configured with complementary-shaped interfacing surfaces, such as the snap-fit surfaces 150 shown. Complementary-shaped interfacing surfaces can provide for lateral coupling between a plurality of the patient's upper and lower teeth, thereby enhancing the distribution of localized lateral impact forces to surrounding tissues.

Accommodating Covering Guards

Figure 9A:
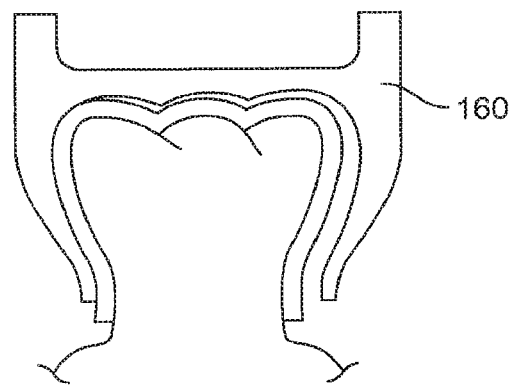
FIGS. 9A and 9B are cross-sectional illustrations of teeth received within incremental positioning appliances that are coupled with accommodating covering guards in accordance with embodiments of the present invention.
Figure 9B:
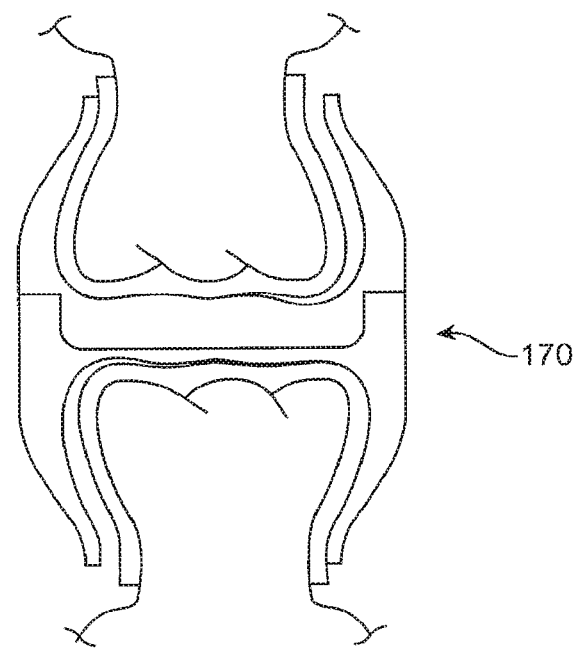

Accommodating covering guards are provided that combine characteristics of an accommodating mouth guard and a covering guard. As such, an accommodating covering guard can be configured to interface with a series of underlying repositioning appliances. FIGS. 9A and 9B illustrate embodiments of accommodating covering guards 160, 170. Because these accommodating guards share characteristics with the accommodating mouth guards and covering guards discussed above, the above discussion applies and will not be repeated here.

Protective Systems

Systems are provided that provide protection against impact-induced injuries during a multi-stage orthodontic treatment. An orthodontic treatment stage can include a series of appliances shaped to reposition a patient's teeth from an arrangement to a subsequent arrangement. A system can include a first accommodating mouth guard for use during a first treatment stage, and a second accommodating mouth guard for use during a second treatment stage. An accommodating mouth guard can include teeth receiving cavities shaped to accommodate a range of positions of a patient's teeth. An accommodating mouth guard can have a shape or material selected to provide protection against impact-induced injury. A system can include a first accommodating covering guard for use during a first treatment stage, and a second accommodating covering guard for use during a second treatment stage. An accommodating covering guard can be configured to interface with a series of repositioning appliances.

A series of two or more of the above discussed protective repositioning appliances, accommodating mouth guards, covering guards, or accommodating covering guards can be used for form a protective system. In the case of protective repositioning appliances or covering guards, the period of use of a particular protective repositioning appliance or covering guard can be generally equivalent to the period of use of an analogous or associated basic repositioning appliance. In the case of accommodating mouth guards or accommodating covering guards, the period of use can be greater that the period of use of an analogous or associated basic repositioning appliance. The period of use for accommodating mouth guards or accommodating covering guards will typically depend on the range of positions accounted for, and the rate that the teeth are being repositioned.

Figure 10:
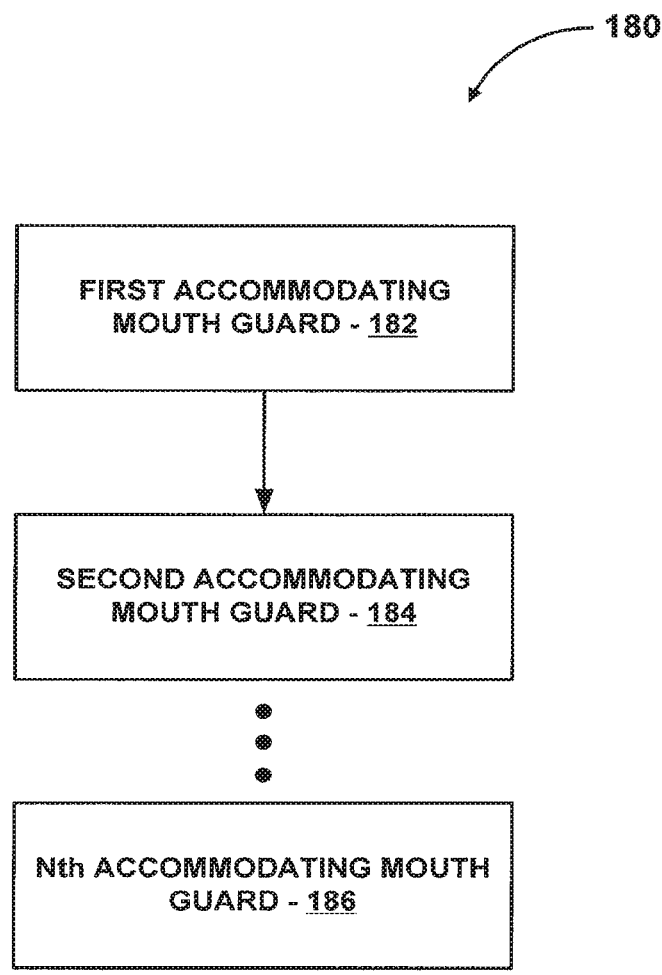
FIG. 10 is a simplified block diagram illustrating a system of accommodating mouth guards in accordance with embodiments of the present invention.
Figure 11:
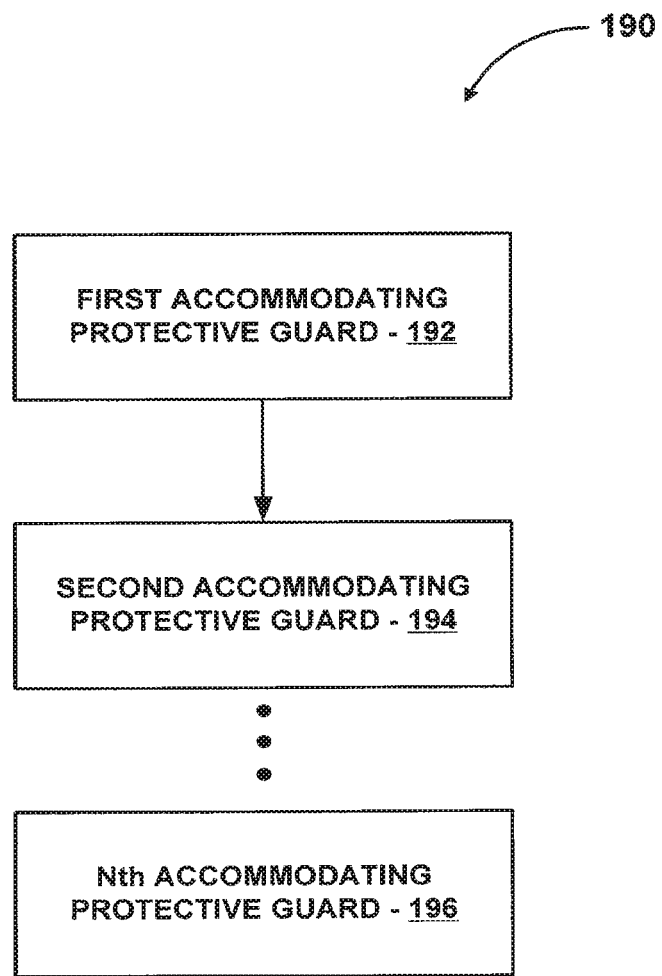
FIG. 11 is a simplified block diagram illustrating a system of accommodating covering guards in accordance with embodiments of the present invention.

FIG. 10 diagrammatically illustrates a system 180 of accommodating mouth guards. The system can include a first accommodating mouth guard 182 that is worn during a first treatment stage during which the patient's teeth are repositioned from a first arrangement to a second arrangement. The system can include a second accommodating mouth guard 184 that is worn during a second treatment stage during which the patient's teeth are repositioned from the second arrangement to a third arrangement. The system can also include additional accommodating mouth guards, such as an Nth accommodating mouth guard 186. Similarly, FIG. 11 diagrammatically illustrates an analogous system 190 of accommodating covering guards 192, 194, and 196.

Fabrication Methods

Figure 12:
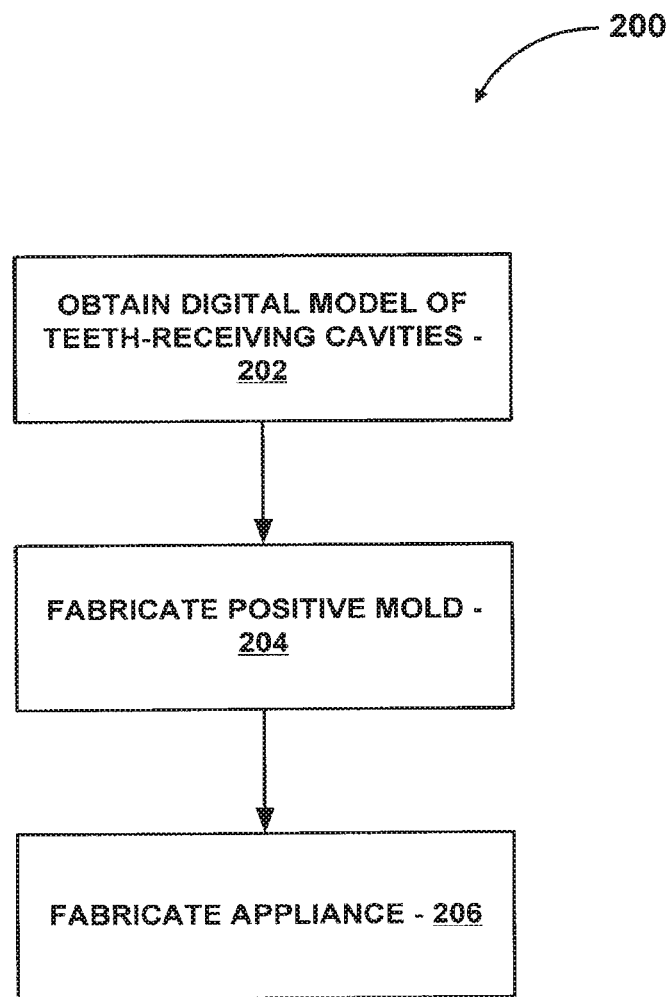
FIGS. 12 and 13 are simplified block diagrams illustrating methods for fabricating protective incremental positioning appliances according to embodiments of the present invention.

FIG. 12 diagrammatically illustrates a method 200 that can be used to fabricate of a protective positioning appliance. In step 202, digital models of teeth-receiving cavities are obtained. These cavities are shaped so that when incorporated into a protective repositioning appliance the appliance exerts resilient forces to the patient's teeth so as to reposition the patient's teeth over time. In step 204, the digital models are used to fabricate a positive mold. The positive mold can be fabricated using a variety of approaches, such as by way of a rapid prototyping machine such as a stereo lithography or digital light projector machine, or also via computer numerical control (CNC) milling. An exemplary rapid prototyping machine is available from 3D System, Valencia, Calif. or EnvisionTEC, Gladbeck, Germany. The rapid prototyping machine can selectively harden a liquid or other non-hardened resin into a three-dimensional structure which can be separated from the remaining non-hardened resin, washed, and used as a positive mold for the appliance. Where such a fabrication method is used, a digital model that includes a negative representation of the teeth-receiving cavities can be prepared from which the positive mold can be fabricated. In step 206, the appliance if fabricated by forming material over the positive mold.

Figure 13:
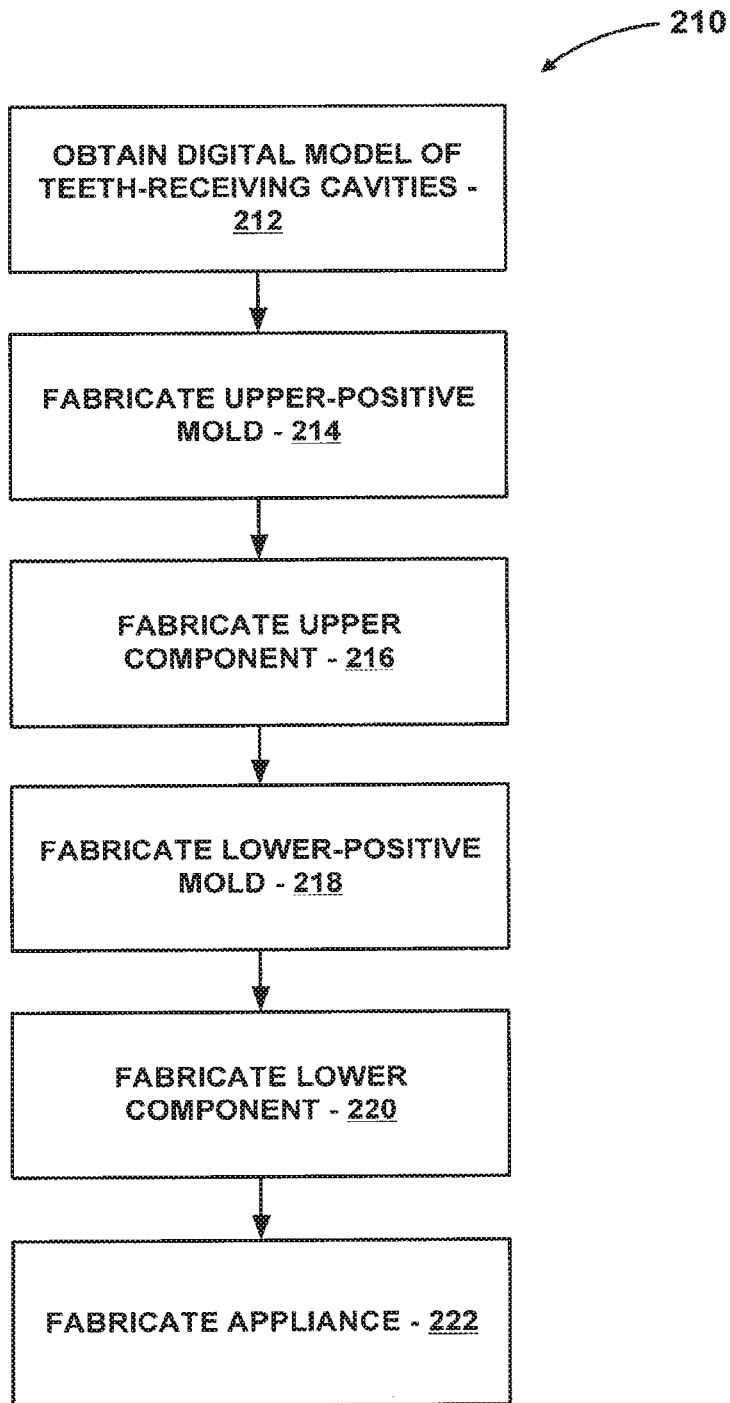

FIG. 13 diagrammatically illustrates a method 210 that can be used to fabricate of a protective positioning appliance having an upper component with upper-teeth receiving cavities, and having a lower component with lower-teeth receiving cavities. In step 212, digital models of the teeth receiving cavities are received. In step 214, an upper-positive mold can be fabricated using the digital models for the upper-teeth receiving cavities as discussed above. In step 216, an upper component is fabricated using the upper-positive mold. In step 218, a lower-positive mold can be fabricated using the digital models for the lower-teeth receiving cavities as discussed above. In step 220, a lower component is fabricated using the lower positive mold. In step 222, the appliance is fabricated using the upper and lower components.

Figure 14:
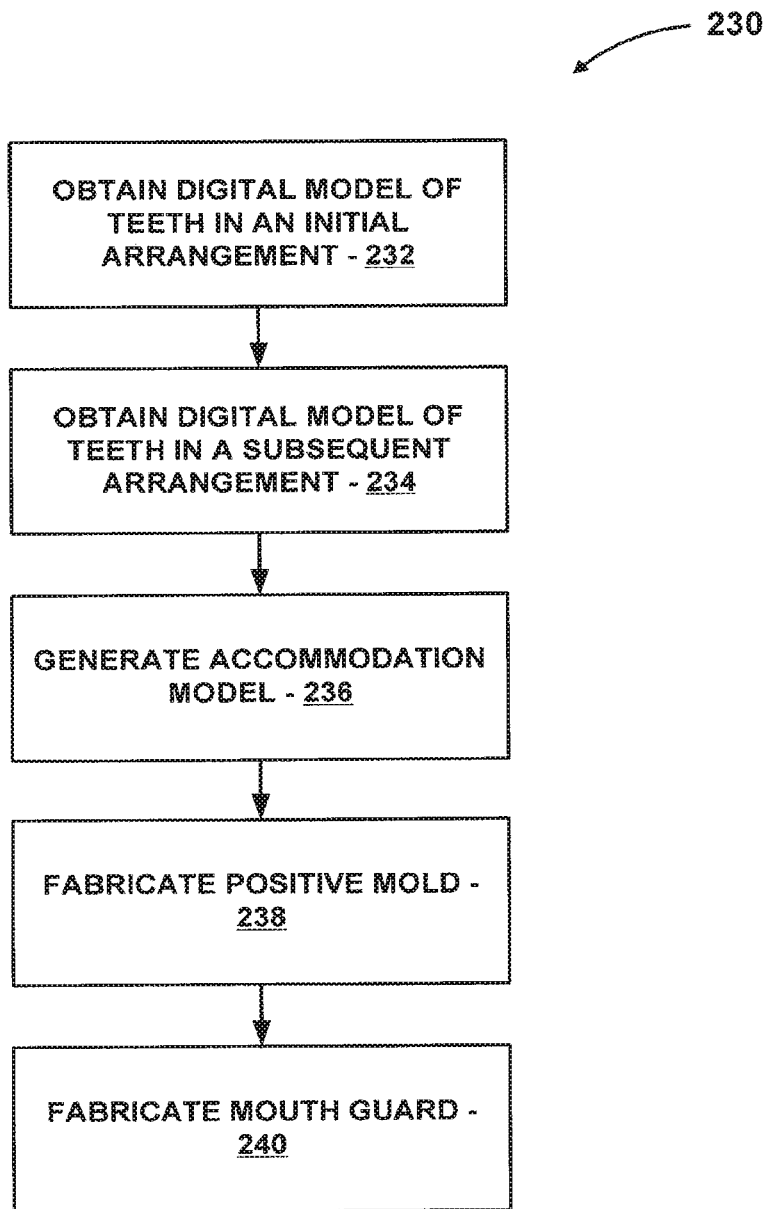
FIGS. 14 and 15 are simplified block diagrams illustrating methods for fabricating accommodating mouth guards according to embodiments of the present invention.

FIG. 14 diagrammatically illustrates a method 230 that can be used to fabricate an accommodating mouth guard. In step 232, digital models of teeth in an initial arrangement are obtained. In step 234, digital models of teeth in a subsequent arrangement are obtained. The initial arrangement and the subsequent arrangements can be the starting and the ending arrangements for which accommodation is to be provided. In step 236, the digital models are combined so as to generate an accommodation model that includes geometry that accommodates the positions of the teeth as they move from the initial arrangement to the subsequent arrangement. Intermediate arrangements between the initial arrangement and the subsequent arrangement can also be used in the generation of the accommodation model so as to more accurately accommodate for intermediate positions of the patient's teeth. A "swept volume" representing the spatial path of each tooth from the beginning to the end within the series can be built in so that the appliance will not interfere with the tooth movement planned during the tooth movement interval for which the guard is designed to accommodate. In step 238, a positive mold is fabricated by using the accommodation model. The positive mold can be fabricated in a variety of ways, such as by using a rapid prototyping machine as discussed above. In step 240, the accommodating mouth guard is fabricated using the positive mold.

Figure 15:
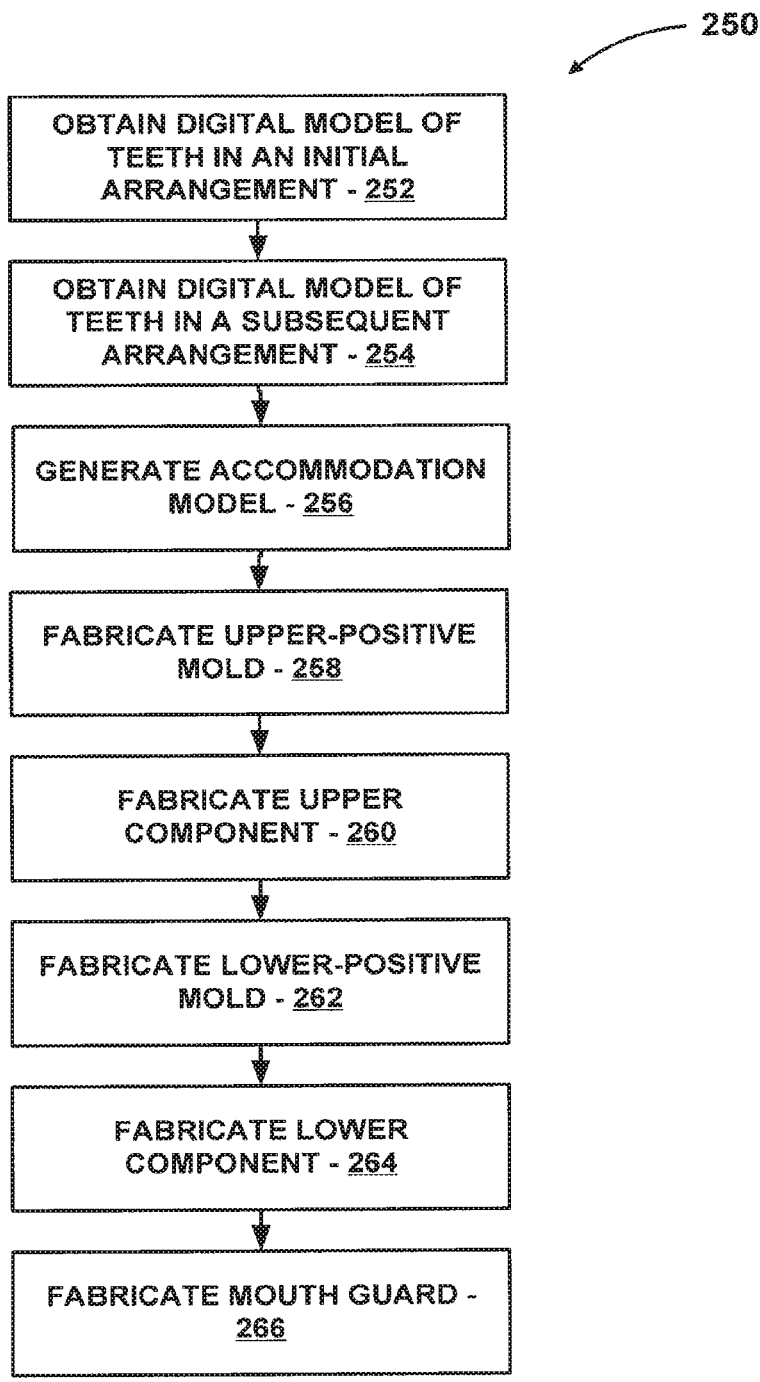

FIG. 15 diagrammatically illustrates a method 250 that can be used to fabricate of an accommodating mouth guard having an upper component with upper-teeth receiving cavities and a lower component with lower-teeth receiving cavities. In step 252, digital models of teeth in an initial arrangement are obtained. In step 254, digital models of teeth in a subsequent arrangement are obtained. In step 256, the digital models are used to generate an accommodation model that includes geometry that accommodates the positions of the teeth as they move from the initial arrangement to the subsequent arrangement. As discussed above, one or more intermediate arrangements can also be used in the formation of the accommodation model so as to more accurately account for intermediate positions of the teeth. In step 258, a upper-positive mold is fabricated by using the accommodation model. In step 260, an upper component is fabricated by using the upper-positive mold. In step 262, a lower-positive mold is fabricated by using the accommodation model. In step 264, a lower component is fabricated by using the lower-positive mold. In step 266, the mouth guard is fabricated from the upper and lower components.

Figure 16:
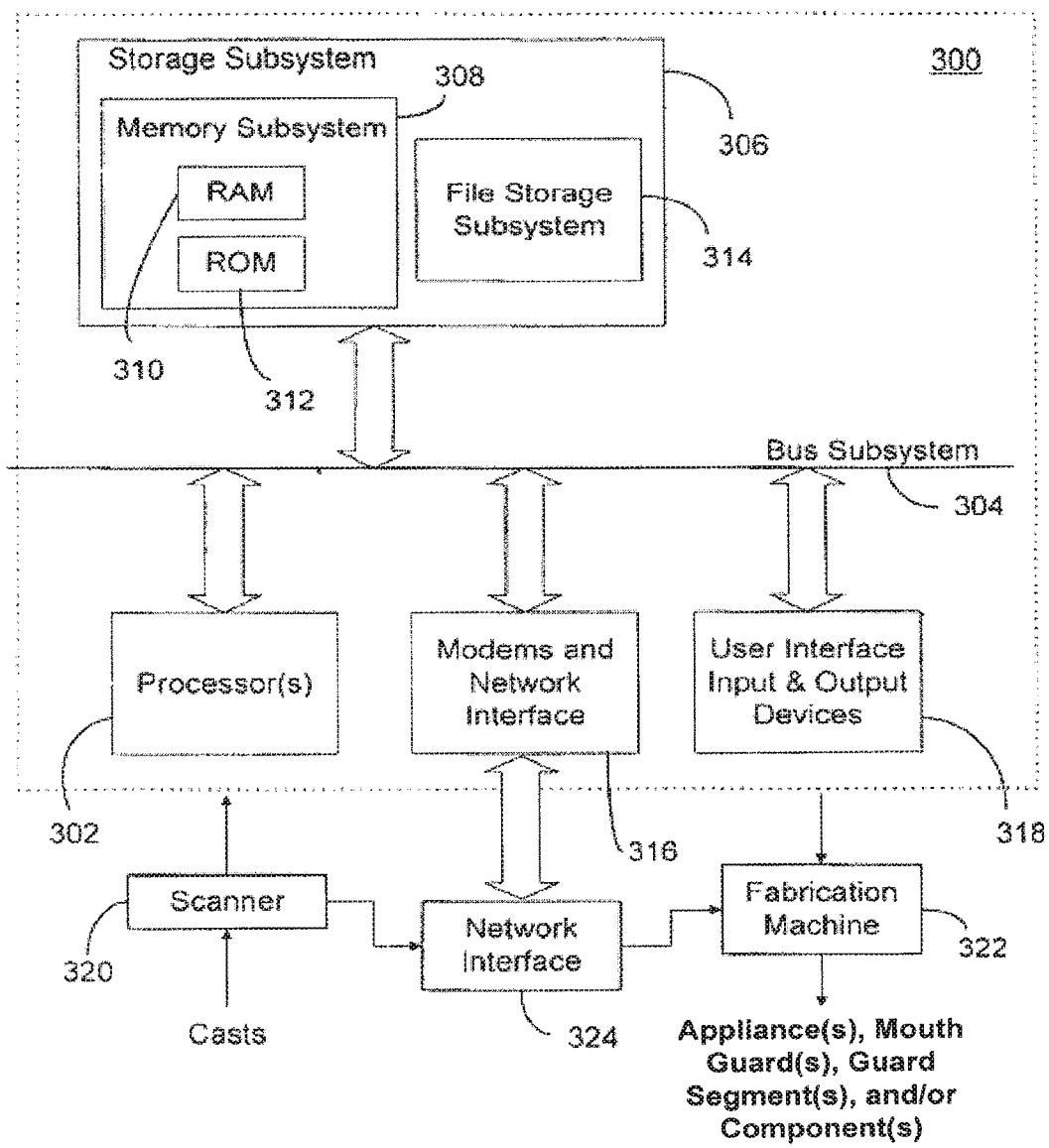
FIG. 16 diagrammatically illustrates a system according to an embodiment of the present invention.

FIG. 16 is a simplified block diagram of a data processing system 300 embodying the present invention. Data processing system 300 typically includes at least one processor 302 which communicates with a number of peripheral devices via bus subsystem 304. These peripheral devices typically include a storage subsystem 306 (memory subsystem 308 and file storage subsystem 314), a set of user interface input and output devices 318, and an interface to outside networks 316, including the public switched telephone network. This interface is shown schematically as "Modems and Network Interface" block 316, and is coupled to corresponding interface devices in other data processing systems via communication network interface 324. Data processing system 300 could be a terminal or a low-end personal computer or a high-end personal computer, workstation or mainframe.

The user interface input devices typically include a keyboard and may further include a pointing device and a scanner. The pointing device may be an indirect pointing device such as a mouse, trackball, touchpad, or graphics tablet, or a direct pointing device such as a touch screen incorporated into the display. Other types of user interface input devices, such as voice recognition systems, are also possible.

User interface output devices typically include a printer and a display subsystem, which includes a display controller and a display device coupled to the controller. The display device may be a cathode ray tube (CRT), a flat-panel device such as a liquid crystal display (LCD), or a projection device. The display subsystem may also provide non-visual display such as audio output.

Storage subsystem 306 maintains the basic programming and data constructs that provide the functionality of the present invention. The software modules discussed above are typically stored in storage subsystem 306. Storage subsystem 306 typically comprises memory subsystem 308 and file storage subsystem 314.

Memory subsystem 308 typically includes a number of memories including a main random access memory (RAM) 310 for storage of instructions and data during program execution and a read only memory (ROM) 312 in which fixed instructions are stored. In the case of Macintosh-compatible personal computers the ROM would include portions of the operating system; in the case of IBM-compatible personal computers, this would include the BIOS (basic input/output system).

File storage subsystem 314 provides persistent (non-volatile) storage for program and data files, and typically includes at least one hard disk drive and at least one disk drive (with associated removable media). There may also be other devices such as a CD-ROM drive and optical drives (all with their associated removable media). Additionally, the system may include drives of the type with removable media cartridges. The removable media cartridges may, for example be hard disk cartridges, such as those marketed by Syquest and others, and flexible disk cartridges, such as those marketed by Iomega. One or more of the drives may be located at a remote location, such as in a server on a local area network or at a site on the Internet's World Wide Web.

In this context, the term "bus subsystem" is used generically so as to include any mechanism for letting the various components and subsystems communicate with each other as intended. With the exception of the input devices and the display, the other components need not be at the same physical location. Thus, for example, portions of the file storage system could be connected via various local-area or wide-area network media, including telephone lines. Similarly, the input devices and display need not be at the same location as the processor, although it is anticipated that the present invention will most often be implemented in the context of PCs and workstations.

Bus subsystem 304 is shown schematically as a single bus, but a typical system has a number of buses such as a local bus and one or more expansion buses (e.g., ADB, SCSI, ISA, EISA, MCA, NuBus, or PCI), as well as serial and parallel ports. Network connections are usually established through a device such as a network adapter on one of these expansion buses or a modem on a serial port. The client computer may be a desktop system or a portable system.

Scanner 320 is responsible for scanning casts of the patient's teeth obtained either from the patient or from an orthodontist and providing the scanned digital data set information to data processing system 300 for further processing. In a distributed environment, scanner 320 may be located at a remote location and communicate scanned digital data set information to data processing system 300 via network interface 324.

Fabrication machine 322 can encompass a range of fabrication machines and methods used to fabricate positive molds, protective positioning appliances, accommodating mouth guards, or covering guards based on data set information received from data processing system 300. In a distributed environment, fabrication machine 322 may be located at a remote location and receive data set information from data processing system 300 via network interface 324.

It is understood that the examples and embodiments described herein are for illustrative purposes and that various modifications or changes in light thereof will be suggested to persons skilled in the art and are to be included within the spirit and purview of this application and the scope of the appended claims. Numerous different combinations are possible, and such combinations are considered to be part of the present invention.

What is claimed is:

1. A system that provides protection against impact-induced injuries during an orthodontic treatment, the system comprising:
    an aligner configured to reposition a first plurality of a patient's teeth on a first jaw of the patient during a stage of the orthodontic treatment from a first arrangement toward a second arrangement different from the first arrangement;
    a first mouth guard configured to protect the first plurality of the patient's teeth on the first jaw of the patient during the orthodontic treatment without applying repositioning forces to the first plurality of the patient's teeth, the first mouth guard comprising:
        a first plurality of cavities configured to receive the first plurality of the patient's teeth on the first jaw of the patient during the stage of the orthodontic treatment, wherein the first plurality of cavities comprise an accommodation envelope providing a swept volume that accommodates the aligner when worn on the first plurality of the patient's teeth, and wherein the swept volume accommodates at least one tooth of the first plurality of the patient's teeth along a spatial path from a first location of the at least one tooth in the first arrangement to a second location of the at least one tooth in the second arrangement; and a first occlusal portion having a first side and a second side opposite the first side, wherein the first side is adjacent to the first plurality of cavities comprising the accommodation envelope providing the swept volume, and the second side includes a first plurality of interfacing surfaces; and a second mouth guard configured to protect a second plurality of the patient's teeth on a second jaw of the patient during the orthodontic treatment, the second mouth guard comprising:

a second plurality of cavities configured to receive the second plurality of the patient's teeth on the second jaw of the patient; and a second occlusal portion connected to the second plurality of cavities, the second occlusal portion comprising a second plurality of interfacing surfaces;

wherein the first plurality of interfacing surfaces is configured to couple to the second plurality of interfacing surfaces so as to laterally couple the patient's first and second jaws to each other to distribute localized lateral impact forces, and wherein at least one of the first or second mouth guards comprises a multi-laminate material comprising a hard outer layer, a soft middle layer, and a hard inner layer.

2. The system of claim 1, wherein at least one of the first plurality of cavities receives a tooth that is not being repositioned during the stage of the orthodontic treatment.

3. The system of claim 1, wherein:
the first occlusal portion is part of a u-shaped tray configured to exhibit an impact-absorbing compliance during an impact forcing the first plurality of the patient's teeth on the first jaw into the second plurality of the patient's teeth on the second jaw.

4. The system of claim 1, wherein at least one of the first or second mouth guards comprises a leash tab.

5. The system of claim 1, wherein at least one of the first or second mouth guards comprises a selected color or ornamental design.

6. The system of claim 1, wherein the first occlusal portion comprises a compliance dependent on one or more of an elasticity of a material of the first occlusal portion, a thickness of the material of the first occlusal portion, or a span coverage of the first occlusal portion.

7. The system of claim 1, wherein the aligner is one of a series of aligners configured to reposition the first plurality of the patient's teeth from the first arrangement toward the second arrangement, and wherein the swept volume accommodates each aligner of the series of aligners when each aligner is worn on the first plurality of the patient's teeth.

8. The system of claim 1, wherein the first plurality of interfacing surfaces and the second plurality of interfacing surfaces comprise complementary coupling features.

9. The system of claim 8, wherein the complementary coupling features comprise snap-fit features.

10. The system of claim 8, wherein the complementary coupling features comprise a plurality of ribs and a plurality of grooves.

11. The system of claim 1, wherein:
the first mouth guard comprises a buccal wall and a lingual wall; and the second mouth guard comprises a buccal recess and a lingual recess, wherein the buccal wall of the first mouth guard is configured to couple the buccal recess of the second mouth guard, and the lingual wall of the first mouth guard is configured to couple to the lingual recess of the second mouth guard.

12. The system of claim 1, wherein the first mouth guard includes a plurality of air passages, each air passage extending from a buccal side of the first mouth guard to a lingual side of the first mouth guard.

13. A system that provides protection against impact-induced injuries during an orthodontic treatment, the system comprising:

an aligner configured to reposition a plurality of a patient's teeth on a first jaw of the patient from a first arrangement toward a second arrangement different from the first arrangement; and a first mouth guard configured to protect the plurality of the patient's teeth, the first mouth guard comprising:
a plurality of cavities configured to receive the plurality of the patient's teeth, wherein the plurality of cavities comprise an accommodation envelope providing a swept volume that accommodates the aligner when worn on the plurality of the patient's teeth, and wherein the swept volume accommodates at least one tooth of the plurality of the patient's teeth along a spatial path from a first location of the at least one tooth in the first arrangement to a second location of the at least one tooth in the second arrangement; and an occlusal portion having a first side and a second side opposite the first side, wherein the first side is adjacent to the plurality of cavities comprising the accommodation envelope providing the swept volume, and the second side is configured to interface with a second mouth guard worn on a second jaw of the patient so as to laterally couple the patient's first and second jaws to each other to distribute localized lateral impact forces.

14. The system of claim 13, wherein the aligner is one of a series of aligners configured to reposition the plurality of the patient's teeth from the first arrangement toward the second arrangement, and wherein the swept volume accommodates each aligner of the series of aligners when each aligner is worn on the plurality of the patient's teeth.

15. The system of claim 13, wherein the occlusal portion is part of a u-shaped tray configured to exhibit an impact-absorbing compliance during an impact forcing the plurality of the patient's teeth on the first jaw into a plurality of the patient's teeth on the second jaw.

16. The system of claim 13, wherein the first mouth guard includes a plurality of air passages, each air passage extending from a buccal side of the first mouth guard to a lingual side of the first mouth guard.

17. The system of claim 13, wherein the first mouth guard comprises a multi-laminate material.

18. The system of claim 13, further comprising the second mouth guard.

19. The system of claim 18, wherein the second side comprises a first coupling feature that is complementary to a second coupling feature on the second mouth guard.

20. The system of claim 19, wherein the first and second coupling features comprise snap-fit features.

* * * * *